US009186317B2

(12) United States Patent
Smyth et al.

(10) Patent No.: US 9,186,317 B2
(45) Date of Patent: Nov. 17, 2015

(54) ACTIVE NANOPARTICLES AND METHOD OF USING

(75) Inventors: Hugh D. Smyth, Albuquerque, NM (US); Marek Osinski, Albuquerque, NM (US); Shayna L. McGill, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 585 days.

(21) Appl. No.: 12/313,847

(22) Filed: Nov. 25, 2008

(65) Prior Publication Data

US 2009/0226521 A1    Sep. 10, 2009

Related U.S. Application Data

(60) Provisional application No. 61/004,324, filed on Nov. 26, 2007.

(51) Int. Cl.
| | |
|---|---|
| A61B 5/055 | (2006.01) |
| A61M 37/00 | (2006.01) |
| A61N 2/00 | (2006.01) |
| A61K 9/00 | (2006.01) |
| A61K 41/00 | (2006.01) |
| A61K 47/48 | (2006.01) |
| A61K 9/50 | (2006.01) |
| A61K 9/51 | (2006.01) |
| A61K 9/70 | (2006.01) |

(52) U.S. Cl.
CPC .......... *A61K 9/0009* (2013.01); *A61K 41/0052* (2013.01); *A61K 47/48853* (2013.01); *A61K 47/48861* (2013.01); *A61K 9/5094* (2013.01); *A61K 9/5115* (2013.01); *A61K 9/7023* (2013.01)

(58) Field of Classification Search
None
See application file for complete search history.

(56) References Cited

U.S. PATENT DOCUMENTS

| | | | |
|---|---|---|---|
| 6,933,373 B2* | 8/2005 | Conseiller et al. ........... 536/23.1 |
| 7,842,281 B2* | 11/2010 | Haik et al. .................... 424/9.3 |
| 7,943,179 B2* | 5/2011 | Little et al. ................... 424/490 |
| 8,449,915 B1* | 5/2013 | Sung et al. .................... 424/489 |
| 2003/0147966 A1* | 8/2003 | Franzen et al. ............... 424/491 |
| 2005/0042753 A1 | 2/2005 | Yang et al. .................... 435/455 |
| 2005/0119725 A1* | 6/2005 | Wang et al. ................... 623/1.15 |
| 2007/0164250 A1 | 7/2007 | Hamad-Schifferli et al. ......................... 252/62.51 |
| 2007/0231393 A1* | 10/2007 | Ritter et al. ................... 424/489 |
| 2007/0243137 A1 | 10/2007 | Hainfeld ....................... 429/9.34 |
| 2007/0258889 A1 | 11/2007 | Douglas et al. ............... 424/1.37 |
| 2007/0264199 A1 | 11/2007 | Labhasetwar et al. ....... 429/9.32 |
| 2007/0270738 A1 | 11/2007 | Wu et al. ........................ 604/46 |
| 2008/0166414 A1 | 7/2008 | Hanes et al. .................. 424/490 |
| 2009/0024019 A1* | 1/2009 | Stein et al. .................... 600/409 |
| 2009/0226526 A1* | 9/2009 | Kurkayev .................... 424/489 |
| 2009/0258073 A1 | 10/2009 | Tishin et al. .................. 424/489 |

OTHER PUBLICATIONS

Zhang, et al. (2009) PLoS Biol., 7(7): e1000155, pp. 1-17.*
Ferrari, e al. (2001) Gene Therapy, 8(18): 1380-86.*
Duguet, et al. (2006) Nanomedicine, 1(2): 157-68.*
Baroli, et al. (Mar. 22, 2007) "Penetration of Metallic Nanoparticles in Human Full-Thickness Skin", The Journal of Investigative Dermatology, 127: 1701-17.*
Mortensen, et al. (2008) "In Vivo Skin Penetration of Quantum Dot Nanoparticles in the Murine Model: The Effect of UVR", Nanotechnology Letters, 8(9): 2779-87.*
http://en.wikipedia.org/wiki/Biofilm, no author, no journal, no volume, no number, no pages, no year, 1 page long.*
Hoet, et al. (2004) "Nanoparticles—known and unknown health risks", Journal of Nanobiology, 2(12): pp. 1-15.*
Izumikawa, et al. (online Feb. 14, 2005) "Auditory hair cell replacement and hearing improvement by Atoh1 gene therapy in deaf mammals", Nature: medicine, 11(3): 271-276.*
Mondalek, et al. (Apr. 7, 2006) "The permeability of SPION over an artificial three-layer membrane is enhanced by external magnetic field", Journal of Nanobiotechnology, 4(4): 1-9 of Epub.*
Dileo, et al. (2003) "Gene transfer to subdermal tissues via a new gene gun design", Human Gene Therapy, 14(1): 79-87.*
Huth, et al. (Mar. 20, 2004) "Insights into the mechanism of magnetofection using PEI-based magnetofectins for gene transfer", The Journal of Gene Medicine, 6(8): 923-36.*
Rosenecker, et al. (2006) "Gene therapy for cystic fibrosis lung disease: current status and future perspectives", Current Opinion in Molecular Therapeutics, 8(5): 439-45, Abstract Only.*
Sumerling, et al. (1982) "Measurements of the Human Anterior Chest Wall by Ultrasound and Estimates of Chest Wall Thickness for Use in Determination of Transuranic Nuclides in the Lung", Radiation Protection Dosimetry, 3(4): 203-210.*
McGill, et al. (2009) "Enhanced drug transport through alginate biofilms using magnetic nanoparticles", Proceedings of SPIE—The International Society for Optical Engineering, 7189(718918): 1-7.*
J. Dobson, Gene therapy progress and propects: magnetic nanoparticle-based gene delivery, Gene Therapy (2006) 13, pp. 283-287.
Wei-Jen Chen, Pei-Jane Tsai, and Yu-Chie Chen, Functional $Fe_3O_4$/$TiO_2$ Core/Shell Magnetic Nanoparticles as Photokilling Agents for Pathogenic Bacteria, Small (2008) x, No. x, 1-7.
M. Dawson, et al., Transport of Polymeric Nanoparticle Gene Carriers in Gastric Mucus, Biotechnol. Prog. (2004), 20 pp. 851-857.

(Continued)

*Primary Examiner* — Robert M Kelly

(57) ABSTRACT

Active multifunctional nanoparticles provide significant enhancement of the efficacy of model therapeutic and gene agents due to increased diffusion and penetration through mucus and biological barriers under the influence of a magnetic field.

16 Claims, 19 Drawing Sheets

(56) References Cited

OTHER PUBLICATIONS

G.L. Burygin, et al., On the Enhanced Antibacterial Activity of Antibiotics Mixed with Gold Nanoparticles, Nanoscale Res. Lett. (2009) 4, pp. 794-801.

Stuart C. McBain, et al., Magnetic nanoparticles for gene and drug delivery, International Journal of Nanomedicine (2008), 3(2), pp. 169-180.

Wei-Chien Huang, Pei-Jane Tsai, Yu-Chie Chen, Functional gold nanoparticles as photothermal agents for selective-killing of pathogenic bacteria, Nanomedicine(2007), 2(6), pp. 777-787.

* cited by examiner

Table 2. Characteristics of magnetic particles used in the magnetic heating experiments

| Name | Size (nm) | Concentration (mg/ml) | Matrix | Functional Group | Specific Loss Potential (W/g) |
|---|---|---|---|---|---|
| beadMAG | 1000 | 100 | Starch cross linked | Sodium phosphate, | 0.324 |
| beadMAG | 500 | 25 | Starch cross linked | Sodium phosphate, | 1.779* |
| fluidMAG-12/AS | 100 | 50 | Polyacrylic acid | Sodium carboxylate | 6.105 |
| fluidMAG-CMX | ~150 | 25 | Carboxymethyl-dextran, sodium | Sodium carboxylate, | 1.950 |
| fluidMAG-D | | 75 | Starch | Hydroxyl groups, | 1.241 |
| fluidMAG-D | 100 | 38 | Starch | Hydroxyl | 0.858 |

Fig. 1a

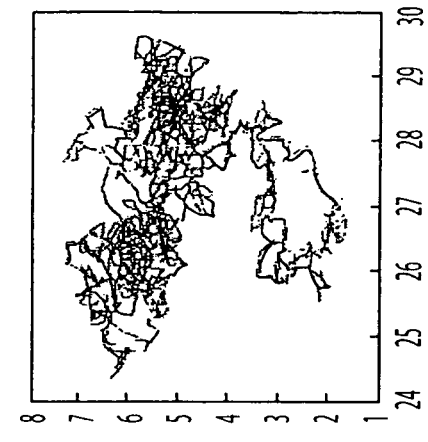
FIG. 6C
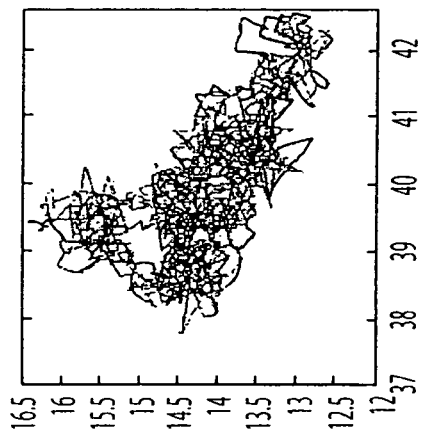
FIG. 6B
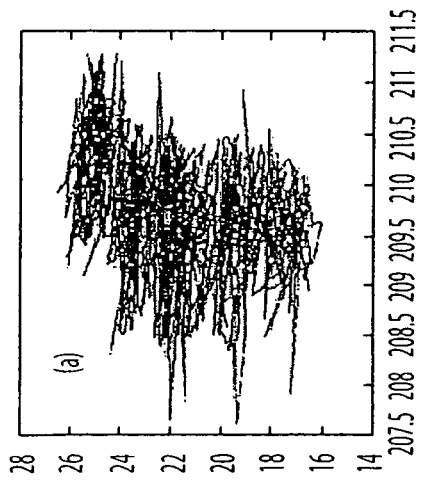
FIG. 6A
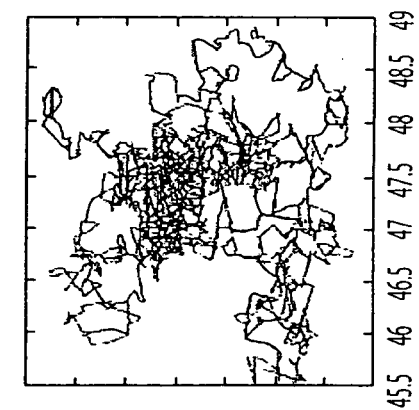
FIG. 8
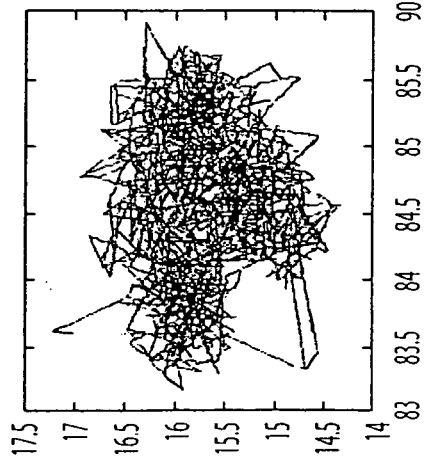
FIG. 7B
FIG. 7A

ACTIVE NANOPARTICLES AND METHOD OF USING

This application claims benefits and priority of provisional application Ser. No. 61/004,324 filed Nov. 26, 2007, the disclosure of which is incorporated herein by reference.

FIELD OF THE INVENTION

The present invention relates to active, multifunctional nanoparticles and methods for using them to enhancing drug delivery and therapeutic efficacy across mucus barriers associated with cystic fibrosis (CF) and lung disease such as tuberculosis, lung cancer, COPD, asthma, pneumonia, etc. as well as other biophysical, biopolymer and biofilm barriers associated with other diseases. They also can be used to enhance transdermal drug delivery.

BACKGROUND OF THE INVENTION

Significant improvements in the treatment of lung diseases (e.g. asthma, COPD, cystic fibrosis (CF)) have occurred over the past 30 years due to drug delivery via inhalation aerosols. However, the efficacy inhaled therapies is dramatically reduced in these patients because of the presence of a viscous mucus transport barrier within the airways, extensive degradation and metabolism of inhaled drug prior to exerting its pharmacological action, and the development of other barriers within the airways due to infection and inflammation, such as in the case of biofilms produced by mucoid *Pseudomonas aeruginosa* colonies. Often drugs or gene vectors cannot reach the intended target before their activity has been reduced or eliminated. Poor transport efficiencies in drug delivery have lead to the failure of therapies including the unattainability of the relatively low efficiencies required for gene therapy success.

Cystic fibrosis is an excellent example of a lung disease in which extracellular barriers prevent effective drug delivery to the lungs. Understanding the genetic defect underlying CF has been described as only half the battle in finding the cure for this disease. This has been evidenced in recent years when, despite great hopes, gene therapy cures have failed to materialize. The underlying cause of CF is a mutation in the gene encoding the cystic fibrosis transmembrane conductance regulator (CFTR) protein. This protein acts as a chloride ion channel and is found in exocrine glands and secretory epithelia. The defective CFTR protein in the respiratory tract reduces the secretion of chloride ions and alters the nature of respiratory mucus. This leads to respiratory complications that include airway obstruction, chronic lung infection, and inflammatory reactions. In nearly all cases, complications in the lungs determine the quality of life/life expectancy of patients.

*Pseudomonas aeruginosa* as the most common bacterial pathogen causing infection in the lungs of people with CF and appropriate antibiotic therapy is vital. Lower respiratory tract infection with *Pseudomonas aeruginosa* (*P. aeruginosa*) occurs in most people with cystic fibrosis. Once chronic infection is established, *P. aeruginosa* is virtually impossible to eradicate and is associated with increased mortality and morbidity'. Antibiotics for exacerbations are usually given IV, and for long-term treatment, via a nebulizer as an aerosol.

Current treatment options include targeted therapy using inhalation aerosols and have been reported since the 1940's. Now, as with asthma, aerosol drug administration in CF appears to have matured and is often used first in the treatment of opportunistic bacterial infections. Inhaled antibiotics have several significant advantages over IV therapy as a large pharmacokinetic advantage is afforded by directly delivering the drug to the airway lumen, avoiding a systemic exposure and potential toxicity. Moreover, inhaled antibiotic therapy administered in the patients' home is significantly cheaper than IV therapy either at home or in the clinic. For *P. aeruginosa*, several clinical trials have compared a nebulized antipseudomonal antibiotic with placebo or usual treatment (oral or IV antibiotics). Lung function was better in the treated group than in a control group. However, resistance to antibiotics increased more in the aerosolized antibiotic treated group than in the placebo. Although outcomes generally favor the aerosol delivery of anti-pseudomonas therapies, it is apparent that drug resistance, through mechanisms including chronic sub-therapeutic concentrations (poor penetration) and mucoid *P. aeruginosa* development, may be responsible.

Another treatment option is gene therapy. By far, gene therapy has been researched more in CF than any other disease due to the feasibility of theoretically correcting the disease by providing a single copy of the CFTR gene to airway epithelial cells. Clinical trials in patients with CF have provided proof-of-principle for gene transfer to the airway epithelium; however, gene delivery is inefficient. Most of the many clinical trials initiated have now been discontinued owing to unsatisfactory primary outcomes. Several studies have shown that extracellular barriers such as mucus and sputum and mucociliary clearance significantly reduce transfection efficiency.

Biophysical barriers to be overcome in treatment of CF are now discussed.

1) Barriers of Aerosol Delivery for CF:

Efficient drug delivery is significantly limited by the multitude of biological and physical barriers in CF. The primary barrier is the viscous mucus layer that results from abnormal secretions. As a consequence of the increase in viscosity/elasticity of the CF mucus, the mucociliary clearance mechanism for removing inhaled particles and microbes is dramatically reduced. This breakdown of the mucociliary escalator results in colonization of the lung and the development of an inflammatory response that imposes additional barriers to successful therapeutic treatment of the airway surface. These include: (1) an extensive inflammatory milieu that causes oxidative or enzymatic degradation of inhaled therapeutics, (2) release of bacterial and endogenous cellular breakdown products and contents (most significantly DNA and lipids), (3) development of mucoid *P. aeruginosa* infections that produce and secrete the exopolysaccharide alginate, and (4) airway obstruction.

2) The Mucus Barrier:

It is well known that the mucus blanket in CF protects the epithelial cells by forming a diffusion barrier for inhaled particles. Respiratory mucus is a complex material, which possesses both flow and deformation rheological properties, characterized by non-linear and time-dependent viscoelasticity and physical properties of adhesiveness and wettability. Viscosity and elasticity are directly involved in the transport capacity of mucus, whereas wettability and adhesiveness contribute to the optimal interface properties between the mucus and the epithelial surface 18. Different biochemical constituents, such as glycoproteins, proteins, proteoglycans, and lipids are involved in the gel properties of respiratory mucus. During bronchial infection and particularly in CF, the loss of water and the increase in macromolecules result in a marked increase in viscosity and adhesiveness responsible for the mucus transport impairment. Phospholipids and associated mucins are also implicated in the interaction between bacteria and epithelial cells.

3) Drug Transport Through Mucus Barriers:

It has been observed that gastrointestinal mucus retards the diffusion of macromolecules. Lipids are a major contributor to reduced diffusion of drugs in native intestinal mucus. In gene therapy, transfection is markedly inhibited in the presence of sputum. Removal of sputum before gene transfer showed increases in efficiency. Pretreatment of sputum-covered cells with DNase also improved gene transfer but efficiencies remained low. It has also been noted that in vivo transfection appears to be a thousand times less efficient than in vitro transfection. This has been attributed to differences in cell characteristics and noncellular barriers. In vivo, the target cells for gene therapy in CF are the submucosal gland cells and the epithelial cells lining the small conducting airways in the lungs. Thus, gene transfection systems must permeate the overlying mucus layer in order to be effective. Compared with normal airway secretions, CF mucus has a higher visco-elasticity because of a high content of actin, serum proteins, DNA, alginate, and rigidifying lipids. These negatively charged biopolymers (mucin, DNA, and alginate) are connected to each other through physical entanglements of their chains and noncovalent interactions. The result is a viscoelastic network that prevents drugs and genes from efficiently being distributed and transported to their target sites.

4) Degradation and Inflammatory Effects:

Neutrophils account for 1% of the inflammatory cell population in epithelial lining fluid in normal individuals, but in CF, neutrophils constitute 70% of the inflammatory cells. Because the neutrophil is remarkably active in the production of degradation enzymes and associated species, the local environment of the CF airways is very inhospitable for therapeutic agents.

5) Barriers Presented by Bacterial Colonization of the Lung:

Although multiple microbial species can successfully colonize the CF lung, robust infections by *P. aeruginosa* eventually dominate the microbial population and become the major contributor to disease severity and life expectancy. The conversion of *P. aeruginosa* microcolonies from a nonmucoid to a mucoid phenotype marks the transition to a more persistent state, characterized by antibiotic resistance and accelerated pulmonary decline. The known and proposed roles of alginate in mucoid infections includes (1) generation of an alginate capsule for direct barrier to phagocytosis and opsonization, (2) immunomodulatory effects, and (3) biofilm related phenomena such as bacterial adhesion and antibiotic resistance. The interference of the exopolysaccharide barrier with antibiotic penetration was demonstrated. Penetration of positively charged hydrophilic drugs, such as aminoglycosides and polypeptides, was markedly inhibited. Even the most aggressive antibiotic treatments may have limited effect on mucoid colonies because of this barrier. Moreover, even sensitive bacteria that do not have a known genetic basis for resistance can have profoundly reduced susceptibility when they form a biofilm. When bacteria are dispersed from a biofilm, they usually rapidly become susceptible to antibiotics, which suggests that resistance of bacteria in biofilms is not acquired via mutations or mobile genetic elements.

6) Airway Obstruction:

Due to chronic infection, mucus accumulation, and airway remodeling, the airways of CF patients can become acutely or chronically obstructed. This can pose significant problems for aerosol therapies that utilize larger aerodynamic particle sizes. Many inhaled antibiotics, for example, are administered using the same design of nebulizer as those used in asthma. As in the case of serious acute asthma attacks, the delivery of aerosols in severely obstructed airways will result in significant decreases in therapeutic doses to the lungs.

Up to now, magnetic nanoparticles have been used in medicine for magnetic separation techniques, as contrast agents in magnetic resonance imaging, for local hyperthermia, or as magnetic targetable carriers for several drug delivery systems. These kinds of particles are routinely produced as commercial contrast agents for MRJ investigations (Combidex®, Resovist®, Endorem®, Sinerem®). These iron oxide nanoparticles exhibit superparamagnetic properties and can be attracted by an external magnetic field. As a result, several in vitro and in vivo studies have shown this to be a promising strategy of localizing chemotherapy agents at cancer tumor sites for cancer therapy.

Similar to magnetic nanoparticles, thermally active nanosystems have been reported for the treatment of cancer via thermal ablation of tumor cells. Several types of metal nanoparticles are capable of converting energy, such as that carried by near-infrared light or an oscillating magnetic field, into heat at a level high enough to kill tumors; i.e. by inducing localized heating in an in vivo situation. Recently, a Phase I clinical trial was completed in patients with recurrent prostate cancer. This study showed that magnetic nanoparticles could be safely administered to humans and produced localized tumor-killing temperatures when stimulated by an oscillating magnetic field. The investigators injected biocompatible magnetic iron oxide nanoparticles directly into the patients' tumors using ultrasound and fluoroscopic imaging to guide the injections. Then, using a magnetic field applicator designed specifically for administering thermal anticancer therapy, the nanoparticles were excited. Each treatment lasted 1 hour and was repeated weekly for 6 weeks. Intracellular hyperthermic treatment of tumors differs from the thermal ablation described above. Intracellular heating has been shown to be incapable of heating the solution or general tumor environment. However, due to the apparent very high temperatures well localized within the cell, cytolysis was induced when an external alternating magnetic field was applied with the biological barriers in CF and how the thermal nanoparticles will interact with the therapeutic agents. It is possible that these systems could be tethered together or be released separately.

As discussed above, CF is characterized by the presence of major barriers to drug and gene delivery. Pre-clinical and clinical studies of gene transfer for CF are ongoing, but these have demonstrated a poor ability to achieve efficient gene transfer through CF mucus. For both gene and drug delivery to the airways of CF patients to be effective, the mucus covering the target cells must be overcome. An object of the present invention is to provide active multifunctional nanoparticles and methods for enabling enhanced drug delivery and therapeutic efficacy by overcoming these biological barriers in CF as well as biophysical barriers in the delivery of therapeutics to the airways of patients with cystic fibrosis and infectious lung disease.

SUMMARY OF THE INVENTION

The present invention provides a method of transporting a treating agent from a region of a patient's body to another distal region wherein a biological barrier exists between the regions. The method involves delivering a plurality of magnetic nanoparticles to the region of the patient's body and providing a magnetic field proximate the distal region in a manner that facilitates transport of nanoparticles and a treating agent associated therewith through the barrier toward the distal region. Various magnetic nanoparticles can be employed in practice of the invention and include surface functionalized nanoparticles where a drug or other treating agent is associated (e.g. attached) to the particle surfaces chemically and/or physically such as by using surface functionalization, bioconjugation, and/or encapsulation schemes using hydrogel particles or coatings. Alternately, magnetic nanoparticles can be employed at a patient's site in combination or in a physical mixture with non-magnetic nanoparticles that have a treating agent associated therewith. Practice of the invention envisions in one embodiment forming channels or tunnels in the barrier as a result of movement of the nanoparticles therethrough to provide open pathways for enhanced drug delivery to the distal region.

In an embodiment of the invention, the magnetic nanoparticles have the treating agent directly associated therewith, for example, by the treating agent being chemically or physically attached to the nanoparticles. In another embodiment of the invention, a mixture of magnetic nanoparticles and non-magnetic nanoparticles is provided at the region such that transport of the magnetic nanoparticles in response to the magnetic field establishes concurrent transport of proximate non-magnetic nanoparticles through the barrier. The treating agent can be associated with the non-magnetic nanoparticles and/or the magnetic nanoparticles. In effect, the non-magnetic nanoparticles are drawn through the barrier toward the distal region by the movement of the magnetic nanoparticles under the influence of the magnetic field.

In practice of embodiments of the invention, the magnetic field gradient can be from about 10 to about 100 T/m (Tesla per meter) for purposes of illustration. The magnetic field gradient can be generated by a permanent magnet or electromagnet magnet (e.g. electromagnetic coil) disposed outside of the patient's body.

The present invention also envisions active, multifunctional nanoparticles and methods for enhancing transport of a treating agent, such as a drug, gene, and/or mucolytic, in and across mucus or other biological barriers associated with cystic fibrosis (CF) and lung disease such as tuberculosis, lung cancer, COPD, etc. as well as other biological (biophysical or /biopolymer) barriers associated with other diseases that include, but are not limited to, diseases of a patient's airway such as passage of the throat, mouth, nose or sinus cavity, of the gastrointestinal tract, of the rectum, of the vagina, as well as infections at these and other regions of the body.

Another embodiment of the present invention involves a transdermal patch that includes magnetic nanoparticles that can be transported across skin under the influence of a magnetic field.

Inhalable microparticles comprising multiple active nanoparticles allow controlled deposition in the airway, avoidance of airway or lung clearance mechanisms, and enhanced transport in CF and other diseases. In an illustrative embodiment of the present invention, inhalable microparticles comprising dispersible, magnetic nanoparticles are employed wherein the nanoparticles have a treating agent thereon. The microparticles each can comprise multiple nanoparticles residing in a carrier matrix, such as a polymer, lipid, or sugar hydrogel, or multiple nanoparticles held by a binding agent in a particle bundle. At least some of the nanoparticles disperse from the microparticles once deposited in the lung and are subjected to a magnetic field gradient generated by a permanent magnet or electromagnet located external of the patient's body in a manner that enhances transport of the nanoparticles across mucous or other biological barriers. The nanoparticles in effect act in a nano-pulley mode under the influence of the static magnetic field. For example, the microparticles can be introduced into the lung interior of the patient by aerosol or other delivery system and then at least partially disperse into individual nanoparticles that are subjected to a local or general magnetic field gradient to enhance transport of the microparticles in and across the mucous barrier toward the distal epithelia at the lung periphery.

In this embodiment, the nanoparticles are introduced as inhalable microparticles wherein each microparticle comprises a plurality of nanoparticles which at least partially disperse after deposition in the lung. The nanoparticles can be sized to optimize heating in an alternating magnetic field, while the overall microparticle diameter and density are suited for aerodynamic lung targeting and deposition, such as in the form of an aerosol. The microparticle can comprise a carrier matrix, such as a polymer, lipid, or sugar (e.g. dextran) hydrogel, in which the nanoparticles reside, or the microparticle can comprise particle bundles of multiple nanoparticles and a binding agent.

In another illustrative embodiment, an electromagnet located outside the patient's body is energized in a manner to generate an oscillating or alternating magnetic field to thermally and/or mechanically activate the nanoparticles. The activated particles in effect act in a nano-knife mode cutting through biopolymers such as DNA strands that cause the muous barrier to be diffusion limiting. The need for bulk heating a lung or other body region can be eliminated with practice of the invention. The alternating magnetic field can be applied when the nanoparticles are proximate the mucous barrier and/or the distal epitheila of the lung. The local particle thermal/mechanical activation due to the presence of the activated nanoparticles may be used in combination with drug therapy to enhance the efficacy and/or distribution of the carried drug and/or facilitate the release of a drug at a particular time or location. The activated nano-knife mode can be employed in addition to, or as an alternative to, the nano-pulley mode described above.

Another embodiment of the present invention provides a method of treating a target site of a patient's body by providing a static magnetic field in a manner to direct drug-bearing (e.g. drug conjugated) conjugated nanoparticles to the target site and then using a mild oscillating magnetic field proximate the target site to control release of a drug at the site without tissue damage.

Still another embodiment of the present invention provides a method of treating a target site of a patient's body by providing drug-bearing (e.g. drug conjugated) nanoparticles in a patient's bloodstream and establishing an oscillating magnetic field proximate the target site effective to release drug from the nanoparticles when they are at the site.

Use of the active nanoparticles as described will facilitate increased drug transport rates, mucus penetration, and antibiotic efficiency in biogels delivered to the lung for treatment of CF and other lung disease such as tuberculosis, lung cancer, COPD, pneumonia, etc.

Other advantages of the present invention will become more readily apparent from the following detailed description taken with the following drawings.

DETAILED DESCRIPTION OF THE DRAWINGS

FIG. 1 is a schematic illustration of active nanoparticles being transported toward epithelia of a lung by a magnetic field generated by a permanent magnet or pancake coil outside the patient's body. The magnetic particles are being pulled as represented by black arched arrows like "nano-pullies" towards the epithelia cell layer through a biopolymer matrix barrier made up of mucin, DNA, biofilms, and bacteria, as represented by the grey track marks and grey ovals, due to the externally applied magnetic field.

Figure 2:
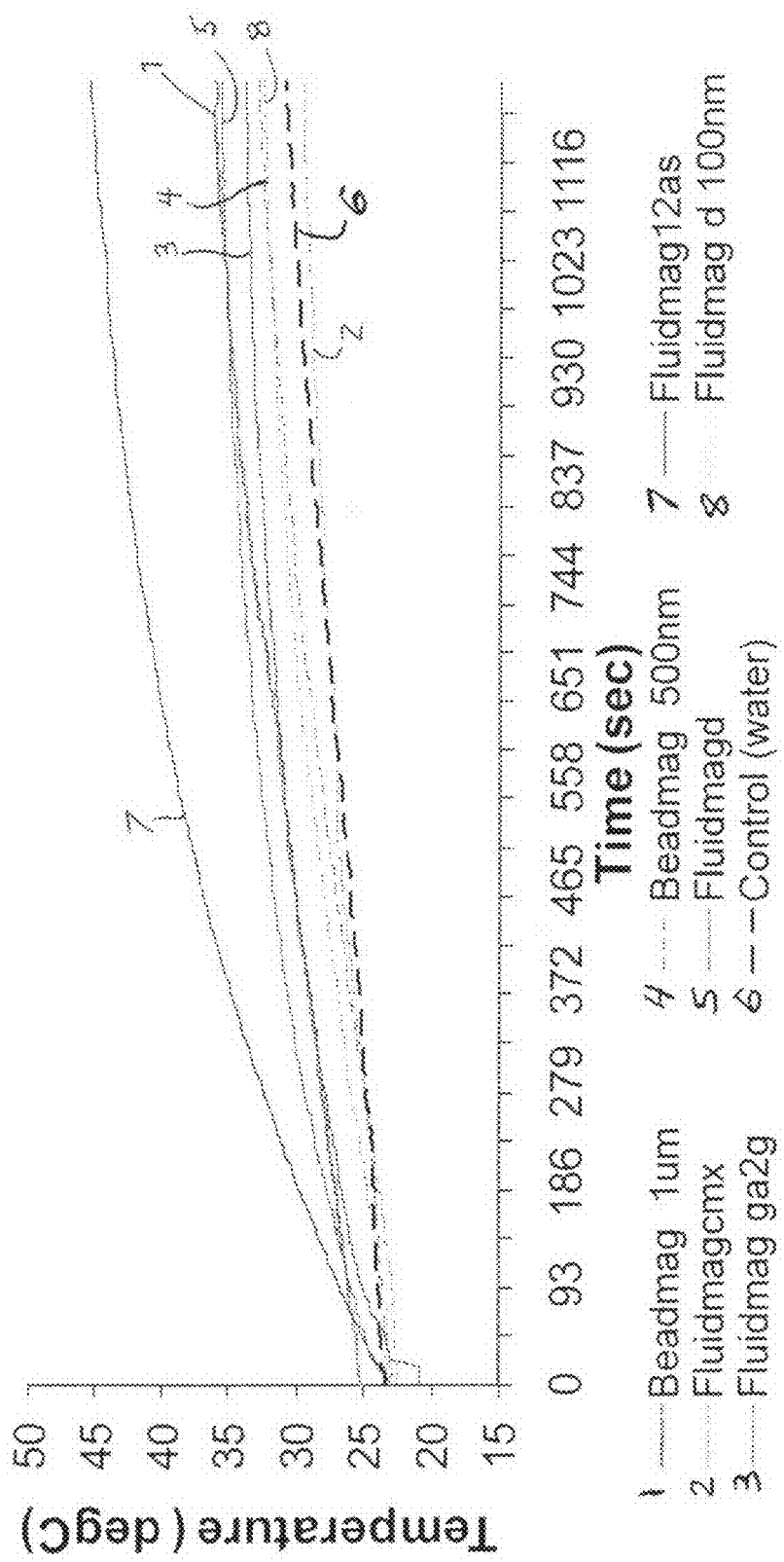
FIG. 2 illustrates heating profiles in degrees C. of magnetic nanoparticles over time in seconds including a control (water) for the various SPIONS tested as shown by different plots.
Figure 2R:
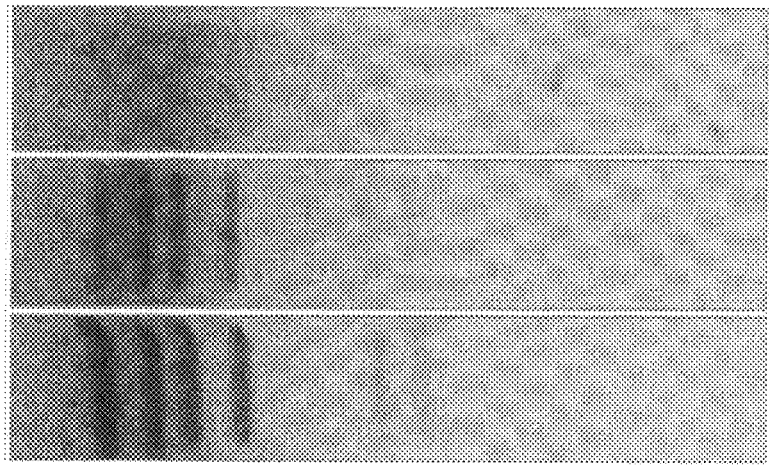
Figure 2B:
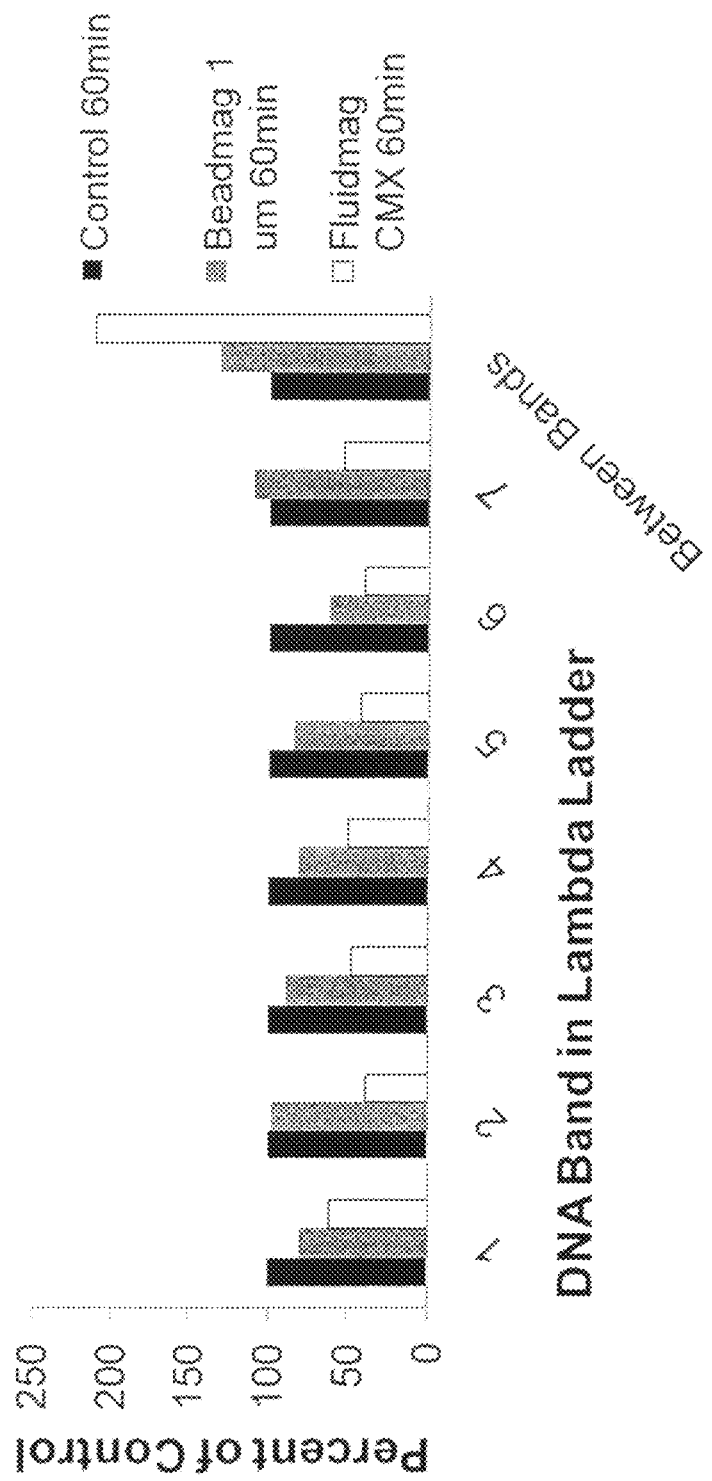

FIG. 2a shows DNA samples exposed to an oscillating magnetic field without SIONs (control-left lane) or with SPIONS (as 1 micron sphere-Beadmag SPIONs (middle lane) or as 100 nm particles-Fluidmag-CMX (right panel) as depicted in an agar gel image. Agarose gel electrophoresis was performed using equal loading of DNA and differences in band and between-band staining was quantified as illustrated in FIG. 2b showing significant decreases in DNA molecular weight and breakage of DNA strands.

Figure 3A:
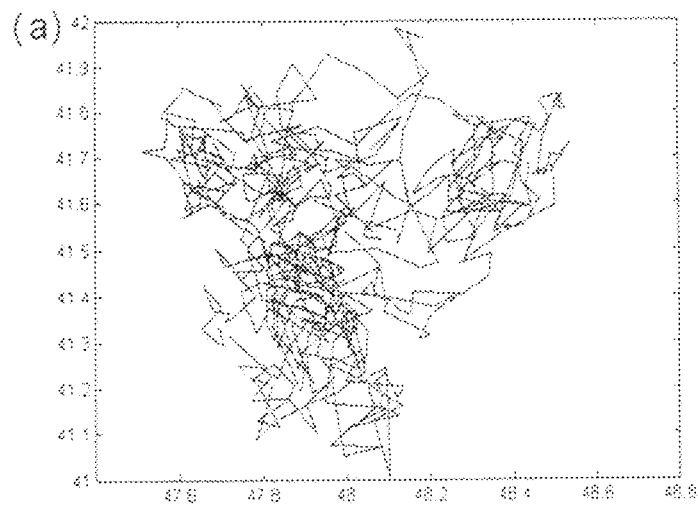
Figure 3B:
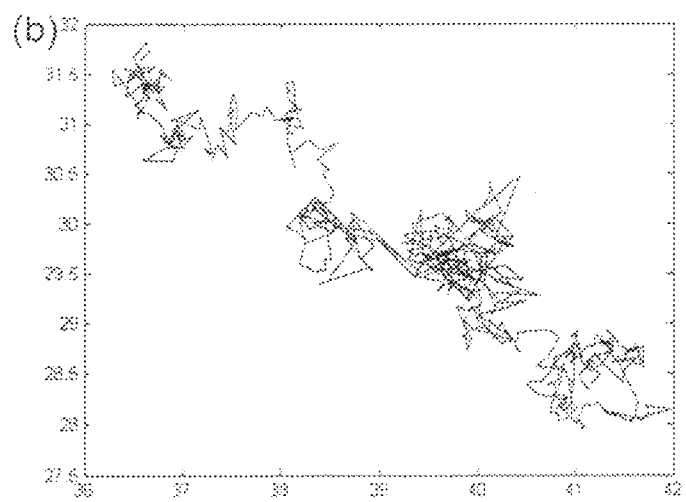

FIGS. 3a and 3b show particle trajectories of Qtracker 655 nm nanoaprticles in DNA samples without an oscillating magentic field (FIG. 3a) and with an oscillating magnetic field (FIG. 3b). Particle motion becomes less hindered upon exposure of the magnetic field. The coordinate units on each axis are in microns.

Figure 4:
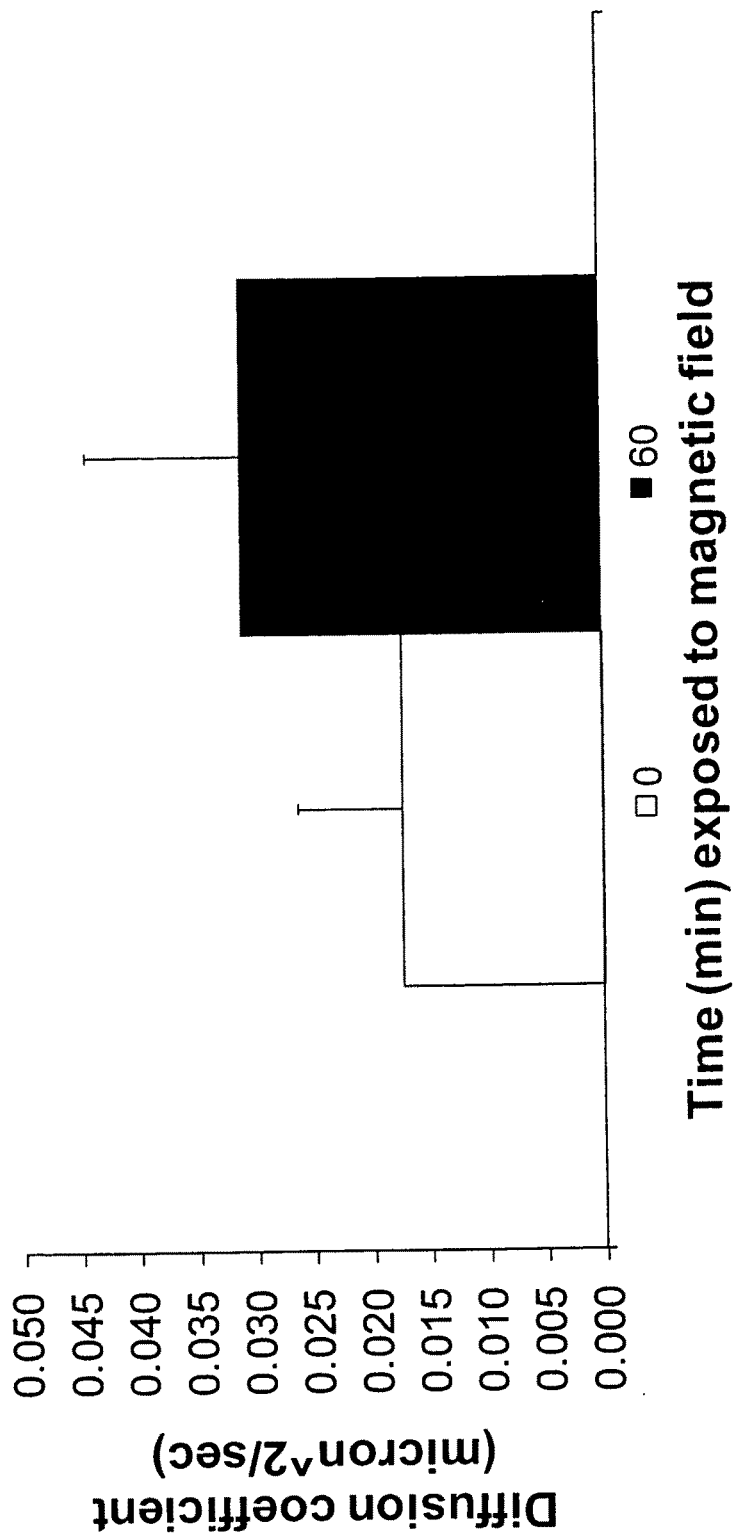

FIG. 4 shows the influence of an oscillating magnetic field on transport of Qtracker 655 nm nanoaprticles in a DNA sample. Significant enhancement in the diffusion coefficient of particles is observed.

Figure 5:
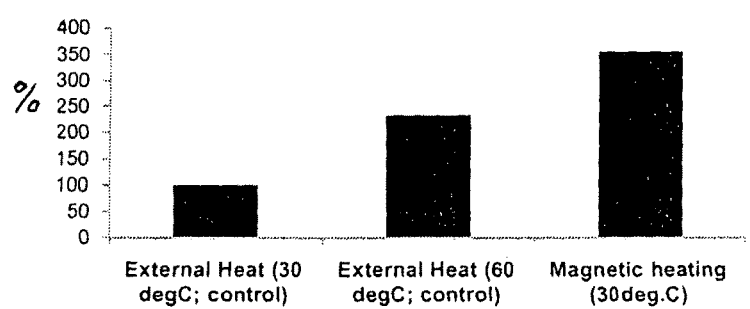

FIG. 5 shows drug, as a percentage of the control, released from drug conjugated nanoparticles at 30 degrees C. with no magnetic field (control), compared to high heat of 60 degrees C with no magnetic field (positive control), and magnetic field treatment to heat nanoaprticles to 30 degrees C.

FIGS. 6a, 6b, and 6c show particle trajectories of Qdot 655 nm particles heated at different temperatures in a alginate biofilm in FIG. 6b (21 degrees C.) and FIG. 6c (34 degrees C.).

FIGS. 7a and 7b show particle trajectories of Qdot 655 nm particles heated at different temperatures in a mucin model in FIG. 7a (21 degrees C.) and FIG. 7b (34 degrees C.).

FIG. 8 shows the diffusion coefficients for Qdot 655 nm particles in the alginate model at the different temperatures shown.

Figure 9A:
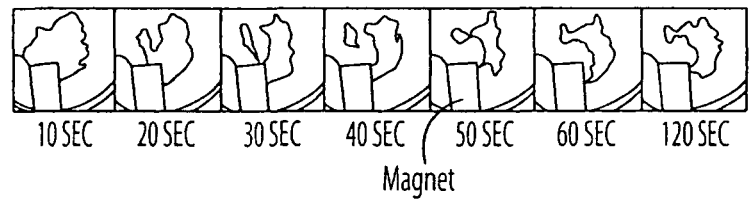
Figure 9B:
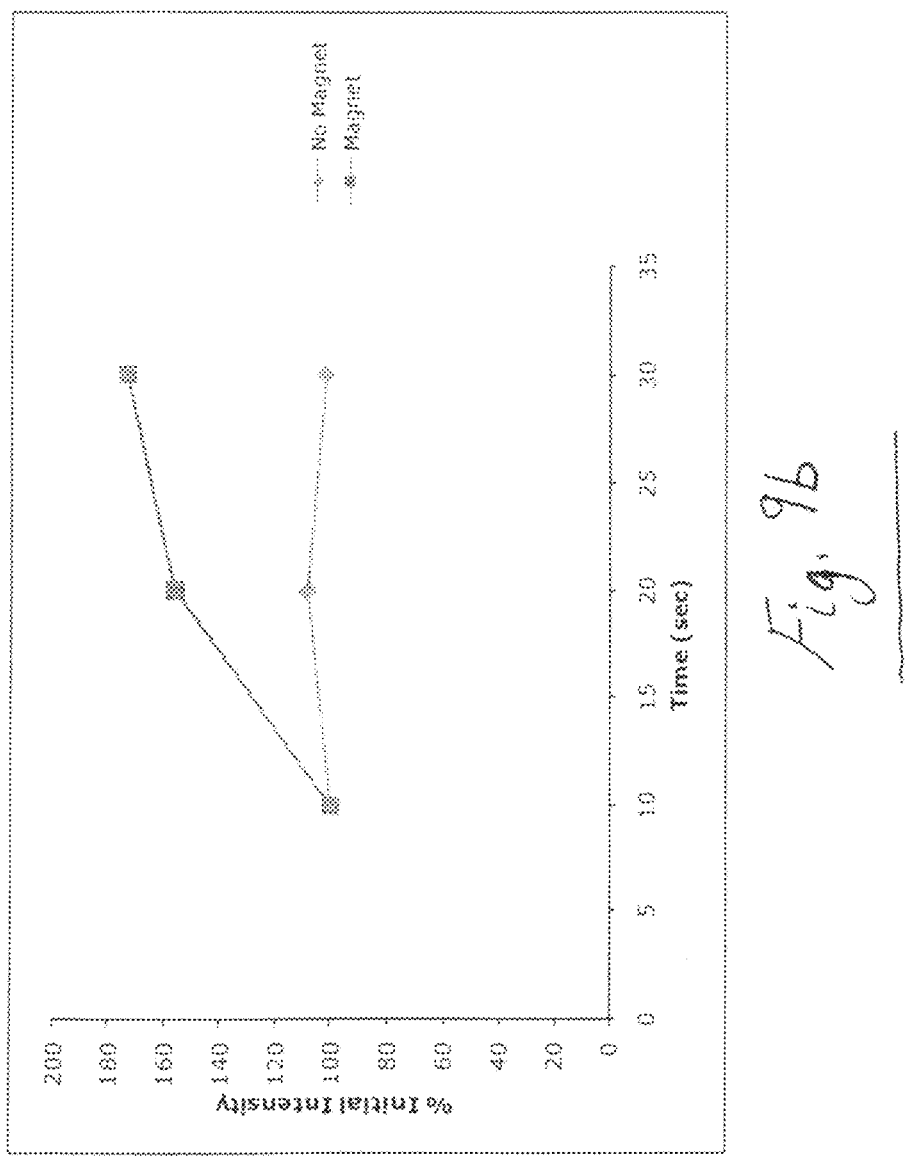

FIG. 9a is a drawing based on a bulk transport photograph montage of the nanoparticle motion over time in the alginate model, while FIG. 9b shows change in intensity over time in the presence of or not in the presence of a magnetic field.

Figure 10:
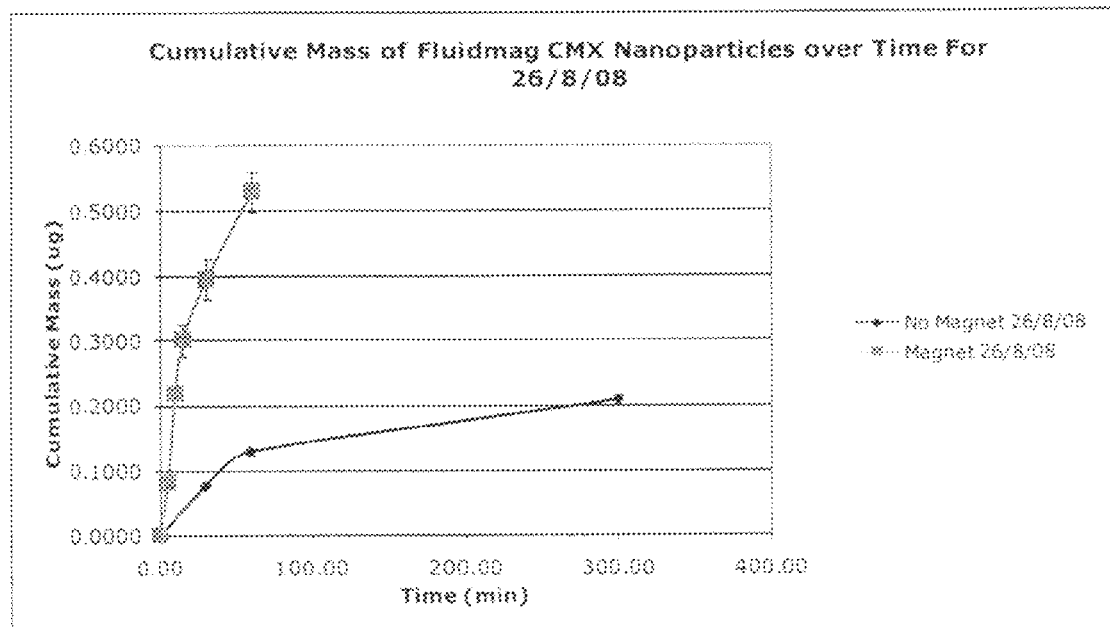

FIG. 10 is a plot of cumulative mass of nanoparticles over time in the presence of or not in the presence of a magnetic field.

Figure 11:
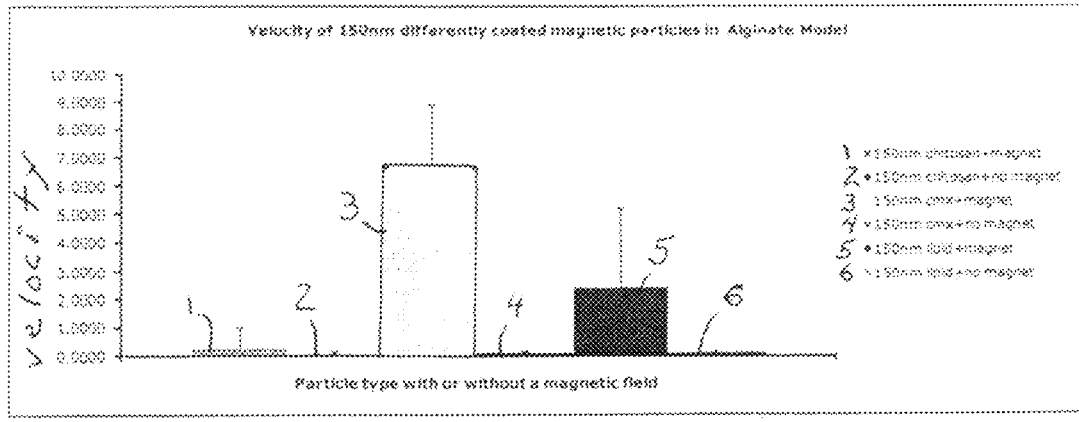

FIG. 11 is a plot of velocity coefficient for different SPIONs shown for 150 nm diameter particles in the alginate model in the presence of or not in the presence of a magnetic field.

Figure 12:
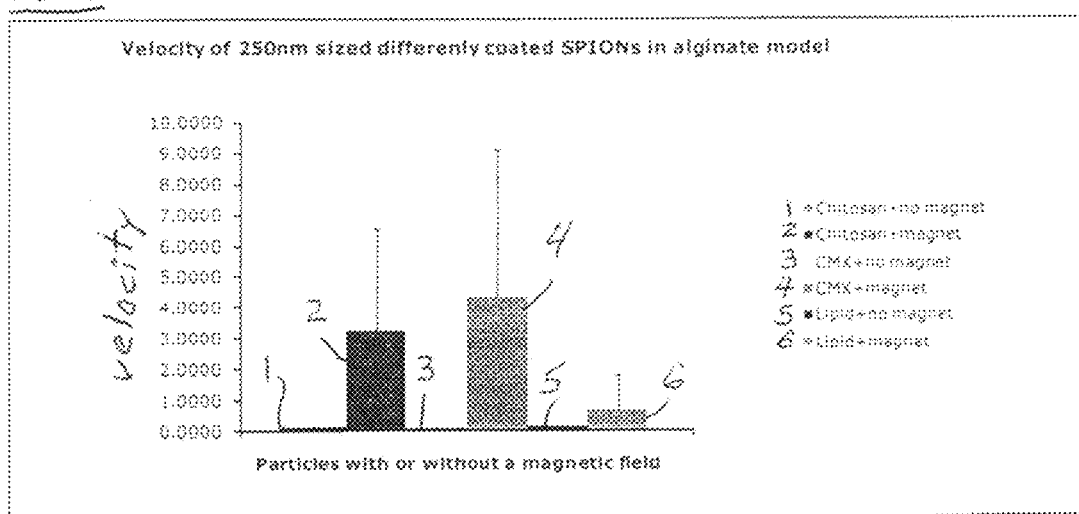

FIG. 12 is a plot of velocity coefficient for different SPIONs shown for 250 nm diameter particles in the alginate model in the presence of or not in the presence of a magnetic field.

Figure 13:
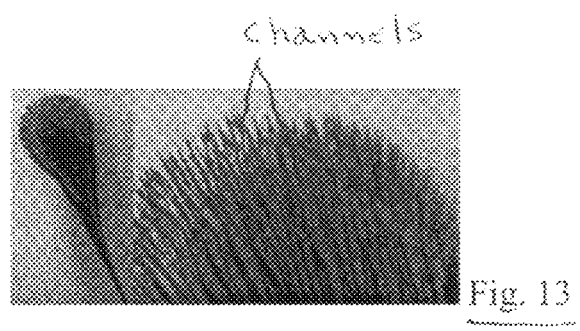

FIG. 13 is a digital camera image of taken during transport of nanoparticles through the alginate model showing channels formed by transport of the nanoparticles through the alginate.

Figure 14:
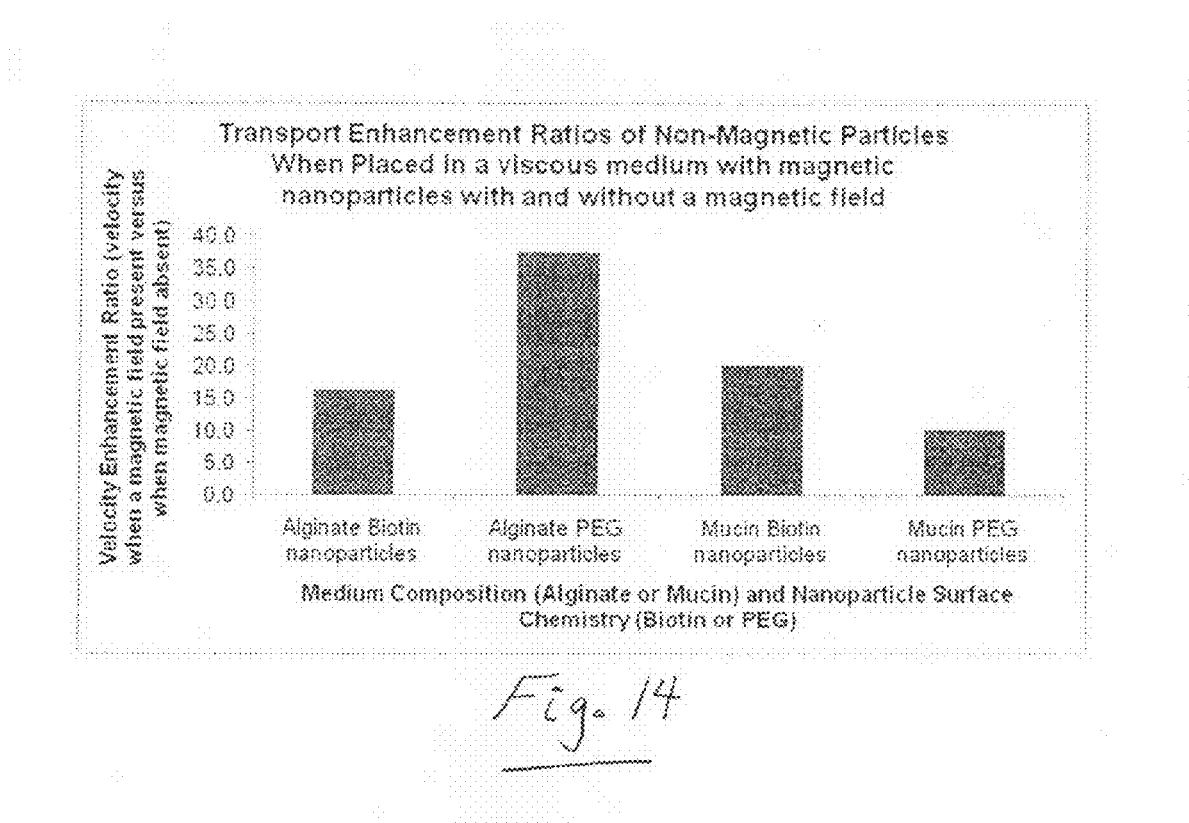

FIG. 14 is a bar graph showing transport enhancement ratios of non-magnetic particles when placed in a viscous medium with magnetic nanoparticles with and without a magnetic field.

Figure 15:
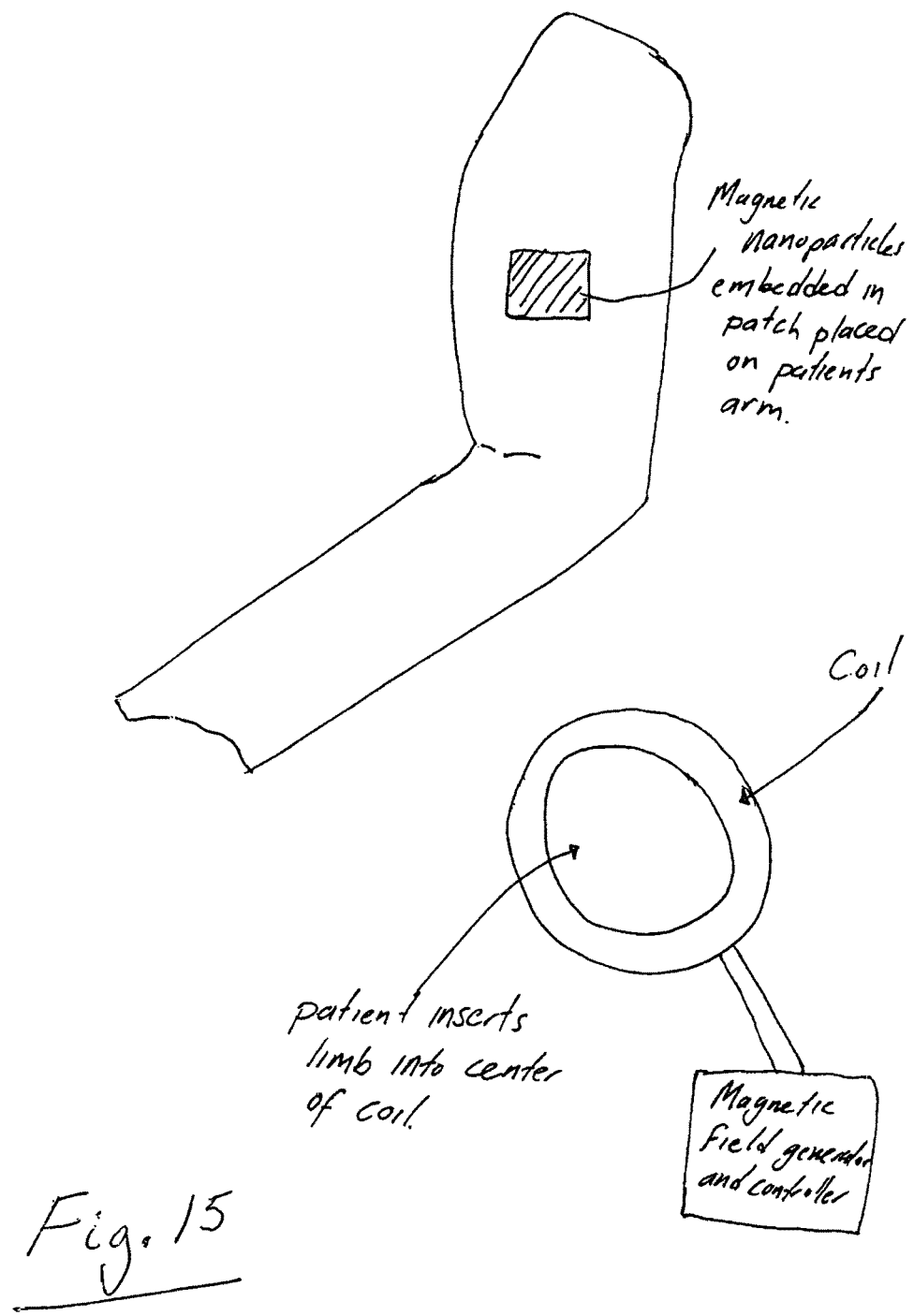

FIG. 15 is a schematic illustration of a transdermal patch and a coil through which a user's arm can be placed.

Figure 16:
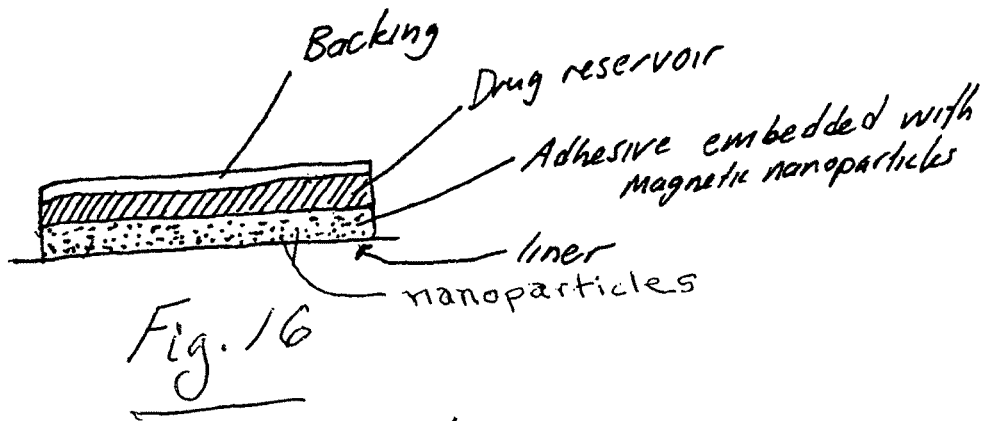
Figure 17:
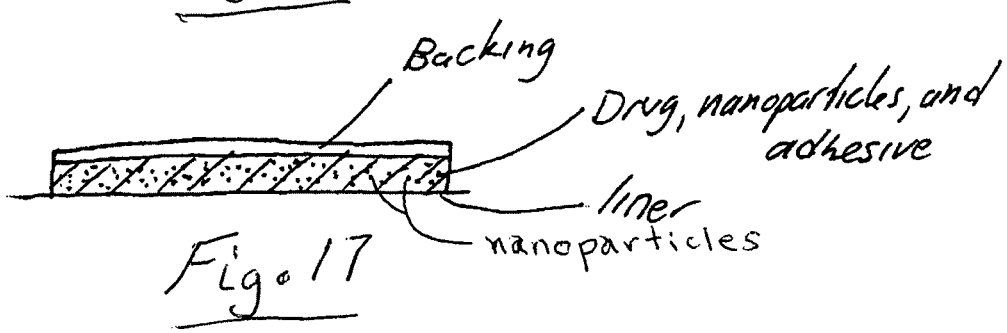
Figure 18:
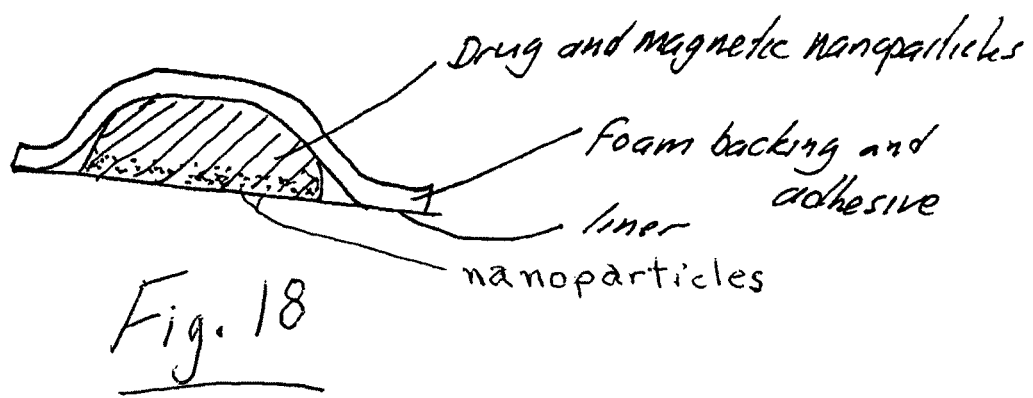

FIGS. 16, 17, and 18 are schematic sectional views illustrating embodiments of transdermal patches pursuant to the invention.

Figure 19:
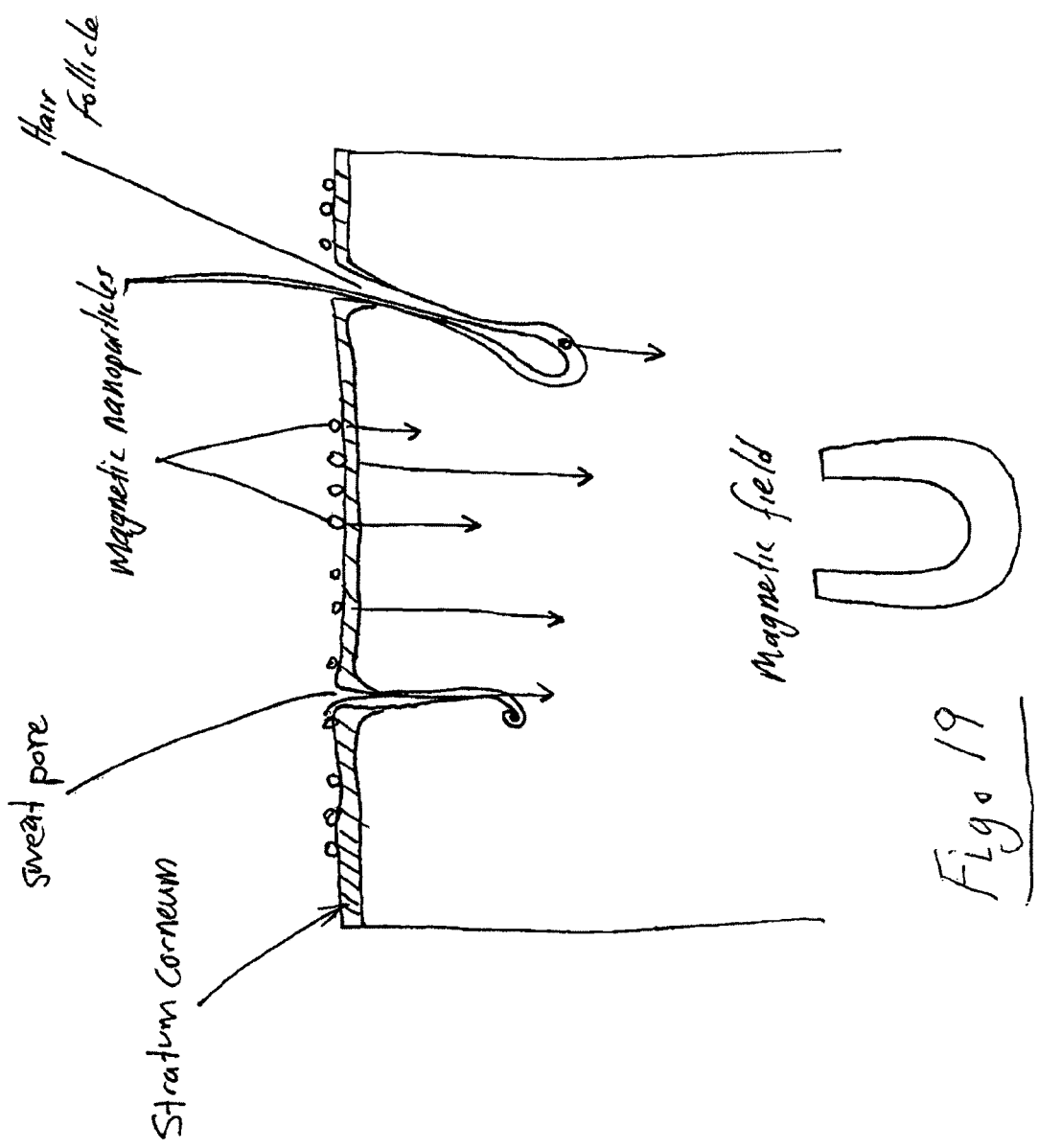
Figure 20:
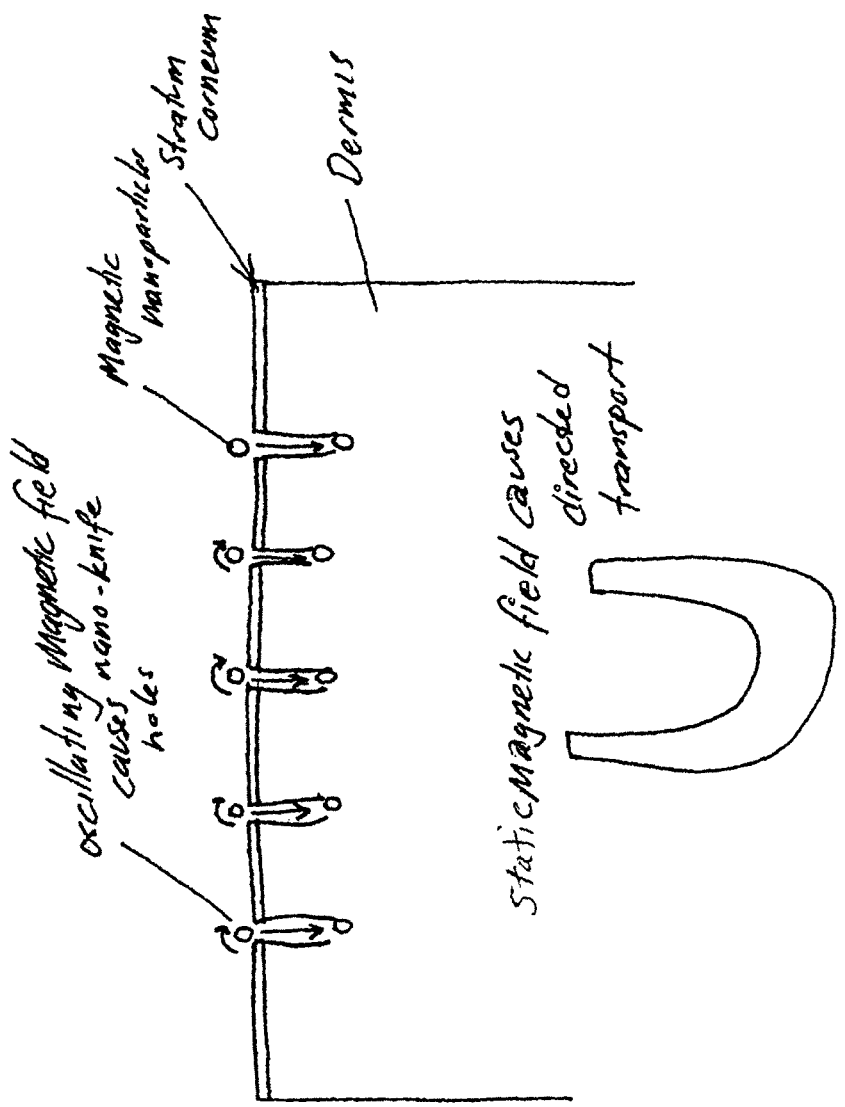

FIGS. 19 and 20 schematically illustrate nanoparticle motion through the stratum coreum of the skin under a static magnetic field, FIG. 19, and under a combined static magnetic field and oscillating magnetic field, FIG. 20.

DESCRIPTION OF THE INVENTION

In one embodiment, the present invention provides active, multifunctional nanoparticles and methods for enhancing drug delivery and therapeutic efficacy across mucus barriers associated with cystic fibrosis (CF) and lung disease such as tuberculosis, lung cancer, COPD, pneumonia, etc. as well as other biophysical barriers associated with other diseases. For example, the invention envisions using active nanoparticles to deliver a drug or treating agent to a patient's airway such as passage of the throat, mouth, nose or sinus cavity or other body passage such as the stomach, intestine, colon, urinary tract, reproductive tract, and the like for transport through a muco or other biological barrier to a distal region in need of treatment. In still other embodiments, the present invention can be practiced for transporting a treating agent from an interior region to a distal region of a patient's body wherein a mucus or other biological barrier exists therebetween by delivering a plurality of nanoparticles to the interior of the patient's body and providing a magnetic field outside of the body in a manner that facilitates transport of nanoparticles through the barrier toward the distal region.

Figure 1:
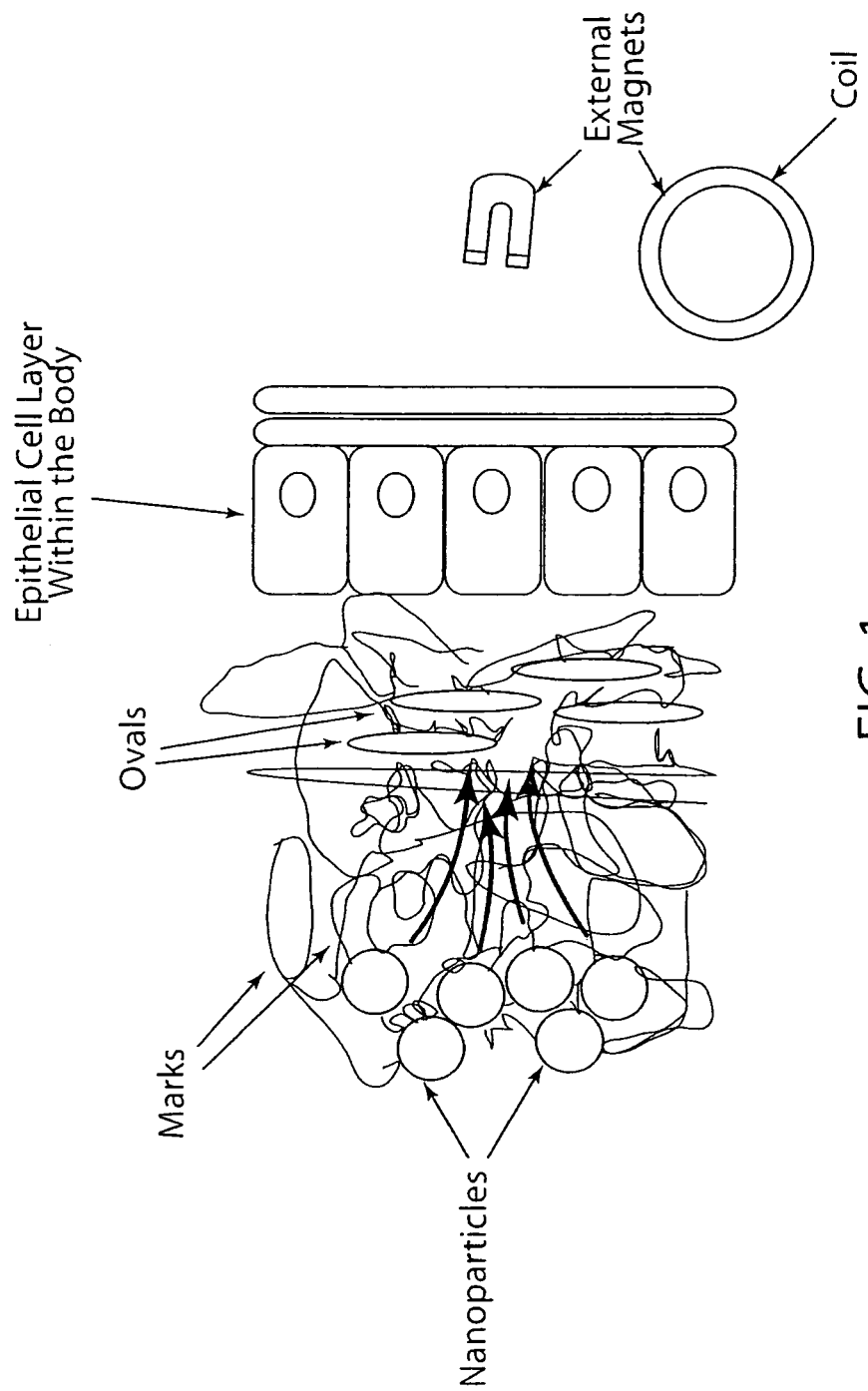
FIG. 1a shows Table 2 providing characteristics of magnetic particles used in the magnetic heating studies.

In another embodiment, the present invention employs inhalable microparticles comprised of a plurality of paramagnetic nanoparticles which have a treating agent associated therewith. The nanoparticles at least partially disperse from the microparticles when in contact with fluids present in the lung to provide at least some individual nanoparticles which are subjected to a magnetic field gradient generated by a permanent magnet or electromagnet (e.g. coil) as shown schematically in FIG. 1 located external of the patient's body in a manner that enhances transport of the particles across a biological barrier that includes, but is not limited to, mucus, biopolymer films, biofilms, skin, and the like. When the magnetic field is a static field, the nanoparticles in effect act in a nano-pulley mode where they are pulled from the interior of the lung where they were deposited toward the distal epithelia of the lung under the influence of the static magnetic field. The magnetic field can exert a torque on the nanoparticles resulting in rotation (e.g. aligning them with the field while spatial inhomogeneities of the magnetic field (e.g. field gradients) exert forces on the nanoparticles resulting in translation motion toward the distal epithelia as described in Example 1. The magnetic field typically is applied at a local distal region of the lung, although a more general magnetic field can be used in practice of the invention.

Various paramagnetic nanoparticles can be employed in practice of the invention and include surface functionalized particles where a drug or other treating agent is associated (e.g. attached) to the particle surfaces chemically and/or physically such as by using surface functionalization, bioconjugation, and/or encapsulation schemes using hydrogel particles or coatings. The nanoparticles are introduced as inhalable microparticles wherein each microparticle comprises a plurality of congregated nanoparticles which disassemble or separate after deposition in the lung. The nanoparticles can be sized to optimize heating in an alternating magnetic field, while the overall microparticle diameter and density are suited for aerodynamic lung targeting and deposition. For example, microparticles having an aerodynamic diameter in the range of about 0.5 to about 5 microns can be used for delivery to the lung. For nasal delivery, the microparticles can be above about 50 microns diameter. The microparticles are comprised of nanoparticles having individual diameters of about 3 to about 1000 nm, more particularly about 5 to about 30 nm. Nanoparticles with core diameter sizes of 5 to 30 nm can be aggregated into larger nanoparticles with polymer binding such that the final aggregate nanoparticle sizes (hydrodynamic diameters) are about 50 to about 200 nm.

The nanoparticles can comprise magnetic nanoparticles commercially produced as commercial contrast agents for MRI investigations under the trademarks Combidex®, Resovist®, Endorem®, Sinerem®). These iron oxide nanoparticles (known as SPIONs) exhibit superparamagnetic properties and can be attracted by an external magnetic field and, therefore, are well suited carrier material for drug targeting systems, and have been shown to be biocompatible with the human body as evidenced by their approval by the United States Food and Drug Administration for human use as an injectable. In practice of embodiments of the invention, iron oxide nanoparticles having a size of 3 to 1000 nm have been used. For in vivo applications, the magnetic nanoparticles of choice are the iron oxide nanoparticles due to their very low toxicity. Magnetic fields exert a torque on magnetic particles resulting in rotation (i.e. aligning them with the field, like a compass needle), while spatial inhomogeneities of the magnetic field (i.e. field gradients) exert forces on magnetic particles resulting in translation in a nano-pulley mode. Other paramagnetic nanoparticles which can be used in practice of the invention include, but are not limited to, gold and indium.

The nanoparticles can be subjected to conjugation and/or attaching of a drug payload using several general methods. For purposes of illustration and not limitation, embedding iron oxide colloids within polymeric fugitive carrier matrices (e.g. dextran, polyethylene glycol) can enhance their physical stability, biological longevity, and also allow co-administration with therapeutic agents co-encapsulated within the polymeric system. Alternatively, therapeutic entities may be linked to nanoparticles via bridging molecules. Surface functionalization and bioconjugation of nanoparticles for targeting and therapeutics will be described below.

Although it is desirable to provide nanoparticles which can be inhaled and are preferentially deposited in the deep lung, efficient generation of nanoparticle aerosols where the particles are not aggregated is very problematic due to the strong van der Waals forces that cause cohesion of particles of this size. As a result, practice of an embodiment of the invention employs microparticles comprised of multiple nanoparticles for lung delivery and controlled release of the nanoparticles. Use of microparticles can be used to increase payload, aerosol efficiency, protect the therapeutic agents, and also to control nanoparticle distribution following deposition in the lung. Once released from the microparticle, a significant advantage of microparticulate SPIONs is the enhanced response that can be achieved to external magnetic fields. Specifically, transport can be significantly enhanced and attained using much lower magnetic field strengths than is needed for smaller SPION loaded particles. Spray dried SPIONs comprising nanoparticles, drug, and in some cases excipient, and polymeric encapsulation of SPIONs in a carrier matrix can be used to make inhalable microparticles. The microparticle carriers of drug should be able to be manipulated for aerodynamic particle size. This will enable lung deposition profiles to be optimized.

For purposes of illustration and not limitation, preparation of respirable microparticles containing the active nanoparticles for lung delivery can use several approaches, such as spray drying and emulsion polymerization. The first approach, via spray-drying, is intended to produce microparticles comprised almost entirely of the nanoparticles and the therapeutic provides immediate release upon deposition in the airways. The second emulsion polymerization approach uses polymeric microparticles such as swellable PEG particles containing nanoparticles. designed to yield microparticles that will have prolonged retention in the airways and control the release of the nanoparticles (by control translocation from lung, protect the therapeutic agent, avoid macrophage engulfment). Details of these methods are set forth in the EXAMPLES below. For purposes of illustration and not limitation, fluidMAG-CMX iron oxide nanoparticles (Chemicell, Berlin, Germany) that contain a dextran coating were diluted in phosphate buffered saline (1.87 mg/mL of nanoparticles). These were aerosalized using a vibrating mesh nebulizer (Omron Micro-air, Ultrasonic Nebulizer, Model NE-U03, Omron Healthcare, Japan) into a drying chamber and particle collection apparatus. Warm dry air was introduced into the chamber with the aerosalized nanoparticles and were allowed to dry as they moved through the apparatus. The dried spherical particles were collected on a glass microfiber filter paper. The microparticles for lung delivery were formed and sized between 0.5 and 3.0 microns.

In another embodiment of the invention, an electromagnet located outside the patient's body is energized in a manner to generate an oscillating or alternating magnetic field to heat or oscillate the paramagnetic nanoparticles (SPIONS) as they pass through the mucus barrier and/or when they are proximate the distal epithelia. The heated or oscillated particles in effect act in a nano-knife mode cutting through biopolymers such as DNA strands that causes the mucus barrier to be diffusion limiting. Although not wishing or intending to be bound by any theory, alternating magnetic fields applied to magnetic nanoparticles can induce heating by several different mechanisms. One mechanism is the rotation of the entire particle (magnetic material plus coating) in a viscous medium, which causes heating due to "friction" between the particle surface and the medium. Another energy loss mechanism involves reorientation of the electron spins in individual magnetic domains while the particle itself remains stationary. This mechanism, known as Neel relaxation, enables magnetic heating of particles that are not free to rotate, e.g., because they are bound to cells by a targeting ligand. Sufficiently large magnetic crystallites (>30 nm) typically consist of more than one magnetic domain, and in these particles, magnetic field-induced rearrangements of the domain boundaries result in energy dissipation. The magnetic heating that can be achieved per unit mass of magnetic material depends on a number of factors, notably the nanoparticle size (both the overall hydrodynamic size and the size of the individual magnetic crystals), the frequency and strength of the alternating magnetic field, and the viscosity of the medium. The nano-knife mode thus may result in magnetically enhanced disruption of the biofilm/mucus diffusion barriers by mechanical breakage of diffusion limiting biopolymer strands (e.g. DNA strands) may be achieved via rotational or lateral damage inflicted by the multi-core magnetic particles, by the Neel mechanism of heating which may also induce thermal scission due to high local temperatures, and/or by other mechanism. The local heating due to the presence of the activated nanoparticles may be used in combination with drug therapy to enhance the efficacy and/or distribution of the drug and/or facilitate the release of a drug from the carrier at a particular time or location as described in Example 1. That is, local heating due to the presence of thermally activated nanoparticles may itself have therapeutic benefits, or heating due to thermally activated nanoparticles may be used in combination with drug therapy to enhance the efficacy or distribution of the drug and/or facilitate the release of a drug at a particular time or location. The thermally active nanoparticles will have the ability to achieve temperatures sufficient for both microenvironment heating (increases in diffusive transport rates) and localized molecular damage (nanoknife functions). The heated nano-knife mode can be employed in addition to, or as an alternative to, the nano-pulley mode described above.

In practicing this embodiment of the invention, nanoparticle size uniformity can be important for maximizing heating, as the optimum operating conditions depend on particle size. For example, for magnetite particles undergoing Neel relaxation, the optimum particle diameter is predicted to be 15 nm, assuming a frequency of about 300 kHz. These can be incorporated into drug-loaded microparticles, which will allow separate optimization of the magnetic nanoparticle diameter (critical for heating) and the overall microparticle diameter and density (critical for deposition in the lung by inhalation).

For purposes of illustration and not limitation, alternating fields of suitable magnitudes and frequencies over samples the size of test tubes or of mice can be easily achieved with home-built coils and modest power amplification (10-100 Watts), provided the circuit is tuned and matched to the power source. In Example 1 below, the magnetic apparatus uses 295 kHz driven by a 10 W or 40 W power amplifier providing typical output of 2-3 kA/m. For applying a uniformly strong oscillating magnetic field over a larger sample volume (e.g., a human thorax) can be achieved using MRI apparatus (using a solenoid or bird-cage coil geometry) such as a commercially-available whole-body hyperthermia system (Magforce Nanotechnologies AG, Germany, 125 kHz, 0-18 kA/m). Larger sample volumes require more power to achieve the same field. In practice of the invention, bulk heating typically will not be required to achieve transport enhancement across biofilms and extracellular diffusion barriers. Specifically, practice of the invention revealed that DNA, a major contributor to CF mucus viscosity and hindered diffusion, can be broken to smaller molecular weight fragments (as analyzed by agarose gel electrophoresis of lambda ladder DNA) when bulk temperatures do not significantly rise above physiological temperatures; e.g. see Example 1. Thus, heating on the nanoscale has the potential to cleave molecules without the need for bulk heating. There are safety benefits to this mode of heating. This also implies that low concentrations of nanoparticles will have the potential to achieve transport enhancement via viscosity modifying behavior through biopolymer fragmentation.

To perform magnetic heating over a smaller region near the surface of a larger sample, a spiral surface coil, FIG. 1, may be positioned over the desired region as frequently employed in clinical MRI probes. In this case, the design rule-of-thumb is that reasonably strong fields are generated within a depth roughly equal to the coil radius. One or more pancake coils could be used to apply an alternating field to the periphery of a particular lobe of the lung for example. The benefit of the smaller coil is that much less power is required to achieve the desired field amplitude compared to a whole-body coil (or, alternatively, a higher field can be achieved in the smaller coil with the same power amplifier).

The present invention envisions providing drug-bearing (e.g. drug conjugated) nanoparticles in a patient's bloodstream and establishing an oscillating magnetic field proximate the target site of the patient's body effective to release drug from the nanoparticles when they are residing at the site. The drug-bearing nanoparticles can be injected or provided in the bloodstream by conventional techniques.

The following EXAMPLES are offered to further illustrate but not limit the invention:

EXAMPLE 1

This Example investigated the potential of magnetic nanoparticles for enhancing drug delivery using a low oscillating magnetic field strength of 3.1 kA/m, which is lower than the field strengths previously used heretofore for other biomedical applications. The ability of magnetic nanoparticles to cause disruption of viscous biopolymer barriers to drug delivery and the potential to induce triggered release of drug conjugated to the surfaces of these particles under these mild oscillating magnetic field conditions was investigated.

The testing showed magnetic nanoparticles can be used to cause significant disruption to viscous biopolymers that cause hindered drug transport and inefficient delivery and also demonstrate the potential to trigger drug release of drug conjugated to magnetic nanoparticle surfaces using these biocompatible magnetic field conditions.

In this Example, magnetic nanoparticles, commonly referred to as superparamagnetic iron oxide nanoparticles (SPIONs), were tested under oscillating magnetic fields to improve diffusive transport of therapeutic agents to enhance drug delivery across biological barriers without destruction of large-scale (mm to cm) regions of tissue. Unwanted heating of surrounding tissue, which might be deemed a mild side effect in the context of a cancer therapy, may not be acceptable in the context of a drug therapy intended for repeated treatment of a chronic illness. The triggered release of drugs from nanoparticle surfaces or the disruption of biopolymer barriers to drug delivery requires significant heating over a much smaller scale such as nanometers to tens of microns.

Several potential biomedical applications of magnetic nanoparticles under weak oscillating magnetic field have been identified. For example, increasing drug diffusion and penetration rates through extracellular barriers may be achieved. There is a significant problem in getting therapeutic agents to their site of action in many diseases due to the presence of biofilms or mucus barriers on epithelia where the drug is administered. In lung diseases such as cystic fibrosis, chronic obstructive pulmonary disease, lung cancer, and asthma, modified or hypersecretion of mucus results in poor efficiencies of drug penetration to target tissues when administered as an aerosol. In infectious diseases that involve bacterial biofilms, the bacteria produce a viscous polysaccharide matrix that can protect the bacteria from antibiotics. In these systems, magnetic nanoparticles can be used to direct transport of drugs associated with the magnetic particles using a static magnetic field to caused accumulation at the target site.

Alternatively, oscillating magnetic fields can induce magnetic nanoparticles to disrupt these biofilms and extracellular barriers. For example in cystic fibrosis lung disease abnormally high viscosities of airway secretions prevent normal lung clearance mechanisms from removing this mucus. As a result bacteria colonize the lung and result in high mortality of these patients at a young age. Inhaled antibiotics are only somewhat successful at removing these infections as the viscous airway environment prevent drug penetration to the site of infection. Moreover, due to the genetic cause of cystic fibrosis, it is highly desirable to develop gene therapy systems that transfect airway epithelia to provide a cure. However, despite many efforts, gene therapy treatments are ineffective due to the poor efficiencies of penetrating to the epithelia that lies beneath the thick airway secretions. One potential application of magnetic particle/AC magnetic fields is to reduce the viscosity of these airway secretions by inducing a nanoknife functionality. For example, magnetic nanoparticles my cause disruption of high viscosity long chain polymers via thermal degradation or by mechanical breakage during oscillating magnetic field application. In cystic fibrosis free DNA in lung secretions results in these high viscosities.

Another potential application of low oscillating magnetic fields is to induce triggered release of drug. This application for drug conjugated magnetic nanoparticles may allow spatial and temporal control of drug delivery.

Methods and Materials:

Magnetic Particles:

Different SPIONs were used depending on the studies. For the temperature profile studies the following particles were obtained from Chemicell (Berlin, Germany): beadMAG, fluidMAG12/AS, fluidMAG-CMX, fluidMAG-D, and fluidMAG-ga2g. Several of these particles were chosen to use in the DNA cleavage studies: 150 nm dia. carboxymethyldextran (CMX) polymer matrix, and 1 μm dia. starch cross linked polymer matrix microparticles were used (fluidMAG-CMX150 nm, beadmag 1 μm dia., Chemicell Berlin, Germany). Single particle tracking studies on fluidMAG-CMX 150 nm dia. nanoparticles were used along with unlabeled, PEG coated quantum dots (Q-tracker 655 nm invitrogen-Molecular Probes, Eugene, Oreg.). Micromod nanoparticles (nanomag®-Dspio, 100 nm dia., Micromod Partikeltechnologie GmbH, Germany) were used for bimane conjugation and triggered release studies. FIG. 1a of Example 1 is a table showing characteristics of the magnetic particles used in the magnetic heating experiments.

Oscillating Magnetic Fields:

The heating circuit consisted of a 95-turn copper coil (L=584 μH, I. D.=10 mm, O.D.=25 mm, C=58 pF). The coil was tuned to 295 kHz and matched to approximately 50 Ohms with a series 440 pF capacitor. Additionally, a 0.7 Ohm resistor was placed in series with the coil to enable the AC or DC current to be monitored. The B/I (field per unit current) ratio of the heating coil was found to be 60 G/A by energizing the coil with a DC current (determined from the voltage drop across the series resistor) and measuring the resulting field along the axis of the coil with a hand-held Gaussmeter (F. W. Bell Model 5070). The oscillating field was generated using a Wavetek 20 MHz Function generator (Model 190) and an EN131 OL broadband (250 KHz-110 MHz) power amplifier (nominal 10 W output). With the tuned/match heating circuit connected, the actual power output of the amplifier was about 40 W, resulting in a measured AC current of 1.3 $A_{p-p}$, corresponding to a magnetic field amplitude ($B_{p-p}/2$) of 39 G (=3.1 kA/m). An EN13100L (nominal 100 W output) with additional attenuation was also used to achieve the same field strength.

Samples were mixed into 1.5 mL microtubes which were placed within a double-walled pyrex thermal shield with a regulated flow of air (380 L/min) between the outer and inner pyrex wall. The shield was used to minimize heating of the sample due to the significant resistive heating of the coil itself. The microtube was also wrapped in pyrex wool to provide additional thermal isolation from the hot coil. The sample, insulation, and thermal shield were then placed within the heating coil, and the oscillating magnetic field was applied over a 30 or 60 min time interval. During exposure to the oscillating field a type T thermocouple (TC-T/4, Dataq Instruments, Akron, Ohio) was placed within the microtube, and continuous temperature measurements were recorded using a Dataq DI-1000-TC thermocouple measurement system (DI-1 000-TC, Dataq Instruments, Akron, Ohio; Windaq Lite Data Acquisition DI-1 000-TC, Dataq Instruments, Akron, Ohio). and processed into an Excel worksheet.

DNA Exposure Studies:

A lambda DNA/Hind III molecular weight marker (Lambda DNA/HindIII Markers, G11711, Promega, Madison, Wis.) of known molecular weight distribution was utilized for evaluation of DNA damage by gel electrophoresis. Each sample contained lambda DNA/Hind III [0.013 mg/mL] and magnetic nanoparticles (Beadmag [7.5 mg/mL]; fluidMAG-CMX [1.87 mg/mL]) was placed within a microtube. The microtubes were then placed within the oscillating magnetic field and exposed for 60 mins, with a 20 μL aliquot removed before exposure representing time 0. The temperature was monitored. As a control lambda DNA/Hind III [0.013 mg/mL] was mixed with dionized water and was placed in the oscillating magnetic field in the same procedure as the test samples. To separate the molecular weight marker from the magnetic nanoparticles for gel electrophoresis samples were run through a magnetic separator (MACS® separation columns, 20μ columns, Miltenyi Biotec, Auburn, Calif.). Additionally the molecular weight marker alone was placed within a heat plate at 60 degC for 60 mins as a further control.

Test samples and controls were analyzed for DNA damage by gel electrophoresis. An agrose gel (UltraPure Agarose-1 000, Invitrogen, Carlsbad, Calif.) was made and formed into a gel apparatus (Owl B1A EasyCast Mini Gel, Thermo Scientific, Waltham, Mass.) with a 10 lane comb. Samples were then mixed with 4 μL loading dye (Blue-Orange 6× Loading Dye, G190A, Promega, Madison, Wis.) and 20 μL was pipetted into individual gel lanes. The gel was exposed to 75 Volts for 1.5 hrs and then placed under UV light for photo exposure.

Single Particle Tracking:

Wide field imaging for single particle tracking for Quantum dots (Qtracker 655 nm, Qdot 655 nm Biotin, Invitrogen-Molecular Probes, Eugene, Oreg.) and magnetic particles (nano-screenMAG chitosan, cmx, and lipid, Chemicell Berlin, Germany) were performed using an Olympus IX71 inverted microscope equipped with a 60×-water immersion. A mercury lamp provided excitation with a 543 nm BP filter. Emission collected by an Andor iXon electron multiplying CCD (emCCD) camera. The back-projected CCD pixel size is 160 nm and images are acquired at 100 frames/s. Typically, a region of interest of 128×128 pixels was selected for imaging. Analysis of the acquired image series was performed as described previously by Lidke et al., "Reaching out for signals: filopdoia sense EGF and respond by directed retrograde transport of activated receptors", J. Cell Biol. 2005: 170 (4): 619-26, the teachings of which are incorporated herein by reference. Images are processed using DIPImage (Delft University of Technology) and tracking routines written in MATLAB (The MathWorks, Inc.) that calculate the center of intensity in a region around the maximum at each time step. Algorithms can explicitly account for the intermittent QD fluorescence, or blinking that. From the trajectories, the mean square displacement (MSD) as a function of time interval (Δt) is calculated. The resulting MSD plot is fitted to the equation for free diffusion: MSD=offset+4DΔt, where MSD is the mean square displacement, D is the diffusion coefficient, Δt is the time interval, and offset is related to the localization accuracy. Localization accuracy of the system is determined by imaging QDots bound to a coverslip for 1,000 frames with 20 ms exposure, which typically yields accurate localization of the particle center of mass to within 12 nm.

Drug Conjugation:

To conjugate the fluorophore bimane amine (Invitrogen Corp., Eugene, Oreg.) that contains one known amine group to the carboxylic acid groups on the magnetic nanoparticles (100 nm dia., 5 mg/ml, Nanomag®-D-spio-PEG-OOOH, Micromod, Rostock-Wamemuende, Germany) an 1Ethyl-3-[3-dimethylaminopropyl]carbodiimide Hydrochloride (EDC) (Pierce Biotechnology, Rockford, Ill.) crosslinking reaction was used. The EDC protocol requires 12.2 mg of N-hydroxysulfosuccinimide (NHS, Pierce Biotechnology, Rockford, Ill.) to be dissolved with 6.5 mg EDC in 2 mL of 0.5M 2-(N-Morpholino)ethanesulfonic acid hydrate (MES) buffer (Sigma-Aldrich, St Louis, Mo.). A 300 µL aliquot of the EDC, NHS solution was pipetted into a vial with 1.5 mL of magnetic nanoparticles and allowed to react for 1 hour at room temperature. The nanoparticle mixture was then washed with 2 mL of 0.1 M MES to remove excess EDC and NHS. The washed mixture was resuspended in a solution of 11.1 mL bimane XX mg/ml in MES buffer and then incubated for 4 hrs at room temperature. To stop the reaction 1 mL of 25 mmol glycine (EMD Chemicals Inc. OmniPur, Gibbstown, N.J.) in phosphate buffered saline (PBS) (Invitrogen Gibco, Grand Island, N.Y.) was added and the solution was allowed to incubate for an additional 30 mins. The nanoparticle solution was then washed with 3 mL of PBS and then resuspended in PBS (3 mL). The newly resuspended nanoparticles were placed in PBS within a Spectra/por dialysis bag (Spectrum Labs Inc, Rancho Dominguez, Calif.) 12-14 kDa for 15 hrs, collecting the suspension liquid four times for further analysis.

Fluorescence intensity analysis was done on the suspension liquid and obtained nanoparticle samples in a 96 black well plate (Type 165305, Nalge NUNC International, Rochester, N.Y.). The analysis was performed using a plate reader Infinite M200 Tecan (Durham N.C.) set at an excitation wavelength of 380 nm and an emission wavelength of 458 nm. Data was collected and compared to a calibration curve using an Excel® template.

Triggered Drug Release Studies:

Bimane conjugated nanoparticles were placed into microtubes at 200 µl volumes. The microtubes were within the Helmholtz coil for exposure to an oscillating magnetic field for 60 mins as described earlier (attaining a temperature of 30 degC). Additional microtubes of sample was placed within water baths at either 30 degC, 60 degC, for 60 mins. Samples were then placed through a magnetic separator MACS Separation Columns 20µ (Miltenyi Biotec Inc., Auburn, Calif.) to retrieve unbound bimane for fluorescence intensity analysis. The analysis was done as described earlier in the conjugation methods.

Microscopy:

A Hitachi 7500 transmission electron microscope (TEM;) was used to obtain TEM micrographs of particles used for the bimane conjugation.

Flourescence images were taken using a Zeiss Axiscope/Epifluorescence microscope with an Axiocam HR color camera. For fluorescence of bimane a DAPI filter set (excitation at 330385 nm) was utilized. Z-stack images were taken with the 100× objective of conjugated particles.

Results:

Magnetic Nanoparticles Generated Heat Using Low External Magnetic Field Strengths The heating response of a range of magnetic nanoparticles to a low oscillating magnetic field were screened over time (30 min) to assess the effect particle characteristics on temperature. Separately, SPIONs with different surface coatings and different sizes were placed within the oscillating magnetic field apparatus that delivered 2.3 kA/m at 295 kHz using a nominal 10 W power amplifier. Temperature increased as a function of time for the panel of SPIONs tested (FIG. 2) and all were greater than the temperature increases in control vials (no SPIONs). From the heating information most SPIONs exhibited similar heating profiles with the fluidMag-12ASL: showing maximal heating over the 30 minute period (about 45 degC).

Magnetic Nanoparticles Caused Disruption to DNA Strands:

The potential of the SPIONs, within an oscillating magnetic field, to cause breakage of viscosity contributing biopolymers (such as DNA that is found in viscous CF airway secretions) was investigated. To detect possible DNA breakage, we examined the molecular weight profiles of DNA before and after oscillating magnetic field treatment in the presence and absence of SPIONs. We used a common "DNA ladder" that has characteristic bands of DNA at certain known molecular weights. Because these samples of DNA are very well defined in terms of DNA polymer length they are excellent probes for strand breakage. Moreover, due to their widespread use in molecular biology, accurate methods to quantify molecular weight and molecular weight changes are readily available. Agarose gel electrophoresis, shown in FIG. 2a, shows that DNA was broken down when magnetic nanoparticles were combined with an alternating magnetic field. DNA band and between-band staining differences were quantified (FIG. 2b) and showed significant decreases in the molecular weights of DNA samples indicating DNA strand breakage. The FluidMag CMX SPIONs caused the significant decreases in all the molecular weights (bands) of the DNA that comprised the "ladder". The staining between bands, which is not found in untreated or heated controls, represents breakage at random points in the DNA strands. Between band densities were increased over 2 times that seen in the control samples with the FluidMag CMX.

Disruption to DNA by Magnetic Nanoparticles Increased Particle Transport:

Although we observed breakage of DNA into smaller fragments due to the presence of SPIONs activated by an oscillating magnetic field, the potential of this breakage to increase drug or particle diffusion required investigation. To see if DNA strand breakage had any effect of nanoparticle transport, we employed single particle tracking techniques to quantify the diffusion coefficients of quantum dots within the DNA mixture before and after magnetic particle/field treatment. The trajectories of particle diffusion before and after the application of a magnetic field (FIGS. 3a and 3b) were used to calculate the particle diffusion coefficients (D, $\mu m^2$/sec). Particle diffusion in DNA samples was approximately doubled by the application of an external magnetic field in the DNA samples compared to the samples that had no field application, FIG. 4. There was some variability in the diffusion coefficients obtained but these differences were statistically significant ($p<0.05$ where p is a level of confidence in statistical testing).

Drug can be conjugated to magnetic nanoparticle surfaces:

The second set of studies investigated drug conjugated SPIONs for triggered release capabilities in low oscillating magnetic fields. Similarly to above investigations, the motivation for these studies was based on the possibility that oscillating magnetic fields may allow for heat or mechanical induced breakage of the drug that is conjugated to the surface of the SPION. We investigated a commonly used conjugation protocol (amide bond formation) that can be performed without use of organic solvents and is amenable to small molecular weight drugs as well as protein and peptide conjugation. This was evaluated using a fluorescent probe, bimane amine as a model drug. Bimane contains a primary amine group for linkage to carboxylic acid groups that are present on many functionalized SPIONs (e.g. MicroMod nanoparticles). This model drug allowed us to validate and quantify drug conjugation to the SPION surface both chemically and visually. We visually confirmed drug conjugation using fluorescence microscopy. TEM images were obtained for unconjugated (controls) and bimane conjugated particles indicated no significant differences in particle appearance. Conjugated particles maintained similar size distribution, shape, and aggregation as unconjugated particles indicating that drug conjugation had no effect of particle stability.

Drug Release can be Triggered from Nanoparticle Surfaces Using Low Oscillating Magnetic Fields:

Amine conjugation through the EDC method has been shown to be thermally stable at normal physiological temperatures. The potential for bond cleavage at temperatures above that of the body might allow for the targeted or triggered release of drug from such a bond. Bimane release from the SPIONs at varying temperatures by either external heating (at 30 or 60 degC) or internal heating by particle exposure to an oscillating magnetic field was observed (FIG. 5) The significantly higher release of bimane during oscillating low magnetic field application demonstrated that the conjugation method could be used for triggered release of drug at physiological temperatures.

This Example illustrates that low oscillating magnetic fields can be used for activating SPIONs in biomedical applications. The levels of nanoparticle heating in these studies were observed to be up to around 35 deg C. This is significantly lower than heating profiles observed typically in hyperthermia treatment protocols for cancer applications. The primary advantages of this mode of operation with magnetic nanoparticles is the lowering of the risk of toxicity due to field strengths and localized tissue damage resulting from high temperatures.

The Example demonstrates that DNA was efficiently broken down to random fragment lengths while bulk temperatures remained low. The breakage of DNA, in the presence of magnetic particles in an oscillating magnetic field, could be due to either thermal and/or mechanical energy dissipated by the particles. These observations lead to exploration of the potential for this effect to enhance drug/nanoparticle transport in viscous barriers to drug delivery.

Specifically, it is well recognized that poor effectiveness of gene therapy in vivo in cystic fibrosis lung disease is caused by the presence of highly viscous airway secretions. These secretions are a complex mixture of biopolymers containing high quantities of mucins and DNA. There is also significant evidence that DNA, released in large amounts into the airway lumen due to inflammatory response, causes the most significant increase in airway secretion viscosity. Therefore, a simplified model of nanoparticles dispersed in a DNA solution was used in this Example to quantify the rates of diffusion of these particles, on a single particle level, before and after the oscillating magnetic field treatment. Consistent with the DNA molecular weight changes due to the magnetic field treatment, we observed that nanoparticles had significantly enhanced transport characteristics following nanoparticle mediated DNA breakage. The quantitative analysis of reductions in DNA strand length is supported by functional differences in particle transport and diffusion in these samples. A two fold increase in diffusion coefficients of quantum dots was observed and illustrates the potential for increasing drug penetration through biofilms and mucus barriers.

This Example also suggested that drugs bound to the surfaces of the SPIONs can be influenced by local heating or mechanical energy induced at these low magnetic fields. This Example demonstrated that magnetic fields could be used to cause triggered drug release. A common conjugation scheme that is biocompatible and widely employed for cellular and molecular biology applications was selected. The amide bonds have also been shown to be thermally labile and relatively stable at physiological temperatures. In this Example, we showed drug release using low oscillating magnetic fields was significantly higher than controls, including the heated sample (60 degC) positive control. Clearly, triggered release of the drug is possible in a targeted manner under this scheme. For example, injected drug conjugated nanoparticles could be accumulated at a target site using a static magnetic field (e.g. at the site of a melanoma). Following this magnetic targeting, a mild oscillating magnetic field could be applied causing drug release into the tumor. Alternatively, an oscillating magnetic field could be placed over the target tissue so that drug is only released from the circulating nanoparticles at the site required. This scheme could potentially be used for antibodies, proteins, peptides, and small molecular weight drugs due to the biocompatible nature of the drug conjugation chemistry.

The present invention demonstrates the potential of magnetic nanoparticles to be utilized for enhancing drug delivery under low magnetic field strengths. Under these biocompatible magnetic field conditions, magnetic nanoparticles can be used to cause significant disruption to biopolymers that cause hindered transport of drug molecules and prevent efficient drug delivery. In addition, drug release can be triggered at these low magnetic fields with minimal heating to the surrounding tissues.

EXAMPLE 2

This example relates to enhanced magnetic nanoparticle transport through models of *Pseudomonas aeruginosa* biofilm and cystic fibrosis mucus.

Presence of viscous mucus transport barrier within the airways and the development of mucoid *Pseudomonas aeruginosa* colonies greatly reduce the efficacy of inhaled therapies in cystic fibrosis (CF) patients. This example involves use of superparamagnetic nanoparticles that exhibit both thermal and magnetic properties to increase transport through in vitro models of CF mucus and alginate biofilms. In vitro CF biological barrier models were modified from the literature to mimic the composition of in vivo samples of CF respiratory secretions and *P. aeruginosa* infections for transport studies. Wide field imaging for single particle tracking was used to quantify transport of particles in in vitro models under different temperature and magnetic presence. Nanoparticle trajectories showed that thermal energy on nanoparticle transport in these models had diffusion coefficient of 10-fold higher than under room temperature conditions. To illustrate the effectiveness of using a magnetic field to enhance transport, single particle tracking experiments were performed using custom-synthesized fluorescent magnetic nanoparticles. From the trajectory plot of particle transport during periods without and with a magnetic field particle diffusion coefficient (D, $\mu m^2/sec$) was increased 170-fold by the application of the external magnetic field in this medium. The application of heat and magnetic field to models of CF mucus/biogels greatly enhanced nanoparticle transport indicating the potential of superparamagnetic nanoparticles to enhance drug delivery in CF patients.

Although multiple microbial species can successfully colonize the CF lung, infections by gram-negative *P. aeruginosa* eventually dominate the microbial population and become a contributor to disease severity. The conversion of *P. aeruginosa* microcolonies from a non-mucoid to a mucoid phenotype marks the transition to a more persistent state, characterized by antibiotic resistance and accelerated pulmonary decline with the development of an alginate biofilm barrier (source). The production of this barrier results in limited antibiotic penetration (source).

The formation of viscous mucus layer that results from abnormal secretions, which protects the epithelial cells from inhaled particles creates another barrier (source). As a consequence of the increase in the visco-elasticity of the CF mucus, the mucociliary escalatory/clearance mechanism for removing inhaled particles and microbes is reduced. Such a reduction results in the colonization of the lung by microbial species and an inflammatory response that additionally forms barriers to efficient therapeutic treatment by increasing the visco-elasitic properties of the mucus (source).

CF is characterized by the presence of biological barriers to drug delivery. For drug delivery to CF patients to be effective, the mucus covering the target cells, as well as the formation of biofilms around *P. aeruginosa* must be overcome. In this Example, we test whether active multifunctional magnetic nanoparticles will be able to overcome such barriers in CF lungs to allow for more efficient drug delivery. To determine this capability we used in vitro models of CF biological barriers to depict known in vivo barriers. Single particle tracking was utilized to depict the efficiency of magnetic pull on nanoparticles through these barriers.

Methods and Materials:

CF Mucin Model:

Pig gastric mucin (type II, lyophilized, Sigma), will be used as a screening model for particle systems. Mucin solutions were prepared by a modified reconstitution procedure as described for use as a model for CF mucus at 20% concentration (see article by Bhat, P G et al. "Drug Diffusion through Cystic Fibrotic Mucus: Steady-State Permeation, Rheologic Properties, and Glycoprotein Morphology", Journal of Pharmaceutical Sciences, 1996; 85 (6): 624-630, the teachings of which are incorporated herein by reference).

Alginate Model:

Concentration for the content of alginate biogels secreted by in vivo samples of *P. aeruginosa* infections for alginate gels was: Alginate concentration will be 2% (w/v) according to as described by Govan, J R, "Microbial pathogenesis in cystic fibrsis: mucoid *Pseudomonas aeruginosa* and *Burkholderia* cepacia", Microbial Rev 1996; 60 (3) 539-74, the teachings of which are incorporated herein by reference, and the bivalent cation concentration (calcium ions) range from 0.5 to 1.8 mM according to Hatch, R A, et al. "Alginate lyase promotes diffusion of aminoglycosides through the extracellular polysaccharide of mucoid *Pseudomonas aeruginosa*", Antimicrob Agents Chemother, 1998; 42(4): 974-7, the teachings of which are incorporated herein by reference.

Magnetic Particles:

Particles were obtain from Chemicell (Berlin, Germany) at either 150 nm or 250 nm dia. sizes. For single particle tracking studies of magnetic nanoparticles fluorescently labeled particles with three different coatings were used (nano-screenMAG-chitosa, -CMX, -lipid 150 nm dia. and 250 nm dia, Chemicell Berlin, Germany). Further tracking studies looking at the influence of magnetic particle motion on Qdots (Qdot 655 nm biotin, Invitrogen-Molecular Probe, Euguene, Oreg.; Qtracker 655 nm, Invitrogen-Molecular Probe, Euguene, Oreg.), only one type of magnetic particle was used (fluidMAG-CMX, 150 nm dia., Chemicell Berlin, Germany).

Single Particle Tracking:

Wide field imaging for single particle tracking for Quantum dots (Qtracker 655 nm, Qdot 655 nm Biotin, Invitrogen-Molecular Probes, Eugene, Oreg.) and magnetic particles (nano-screenMAG chitosan, cmx, and lipid, Chemicell Berlin, Germany) was performed using an Olympus IX71 inverted microscope equipped with a 100°—oil objective. Excitation was provided by a mercury lamp with a 543 nm BP filter. Emission collected by an Andor iXon electron multiplying CCD (emCCD) camera. The backprojected CCD pixel size is 160 nm and images are acquired at 100 frames/s. Typically, a region of interest of 128×128 pixels was selected for imaging. Analysis of the acquired image series will be performed as described previously 91. Images will be processed using DIPImage (Delft University of Technology) and tracking routines written in MATLAB (The MathWorks, Inc.) that calculate the center of intensity in a region around the maximum at each time step. These algorithms can explicitly account for the intermittent QD fluorescence, or blinking that. From these trajectories, the mean square displacement (MSD) as a function of time interval ($\Delta t$) will be calculated. The resulting MSD plot is fitted to the equation for free diffusion: $MSD=offset+4D\Delta t$, where MSD is the mean square displacement, D is the diffusion coefficient, $\Delta t$ is the time interval, and offset is related to the localization accuracy. Other modes of motion can be determined from these plots, including velocity. Localization accuracy of the system is determined by imaging QDots bound to a coverslip for 1,000 frames with 20 ms exposure, which typically yields accurate localization of the particle center of mass to within 12 nm.

Effect of Thermal Heating on Particle Diffusion:

Samples of 200 μL of in vitro models with 10 μL of Qdot 655 nm were placed in 8-well transwell plates for single particle tracking. The objective lens was heated by an external heater, which transferred heat to the sample. Tracking was performed on each sample before and during heating.

Directed Motion of Particles:

In vitro models were mixed with about 10 μL of magnetic particles (nano-screenMAG-chitosan, -CMX, -lipid) and aliquot into 8 well transwell plates. Images were taken for single particle tracking analysis with or without the presence of a neodymium-iron-boron permanent magnet having a volume of one cubic centimeter placed outside each individual well.

Influence of Magnetic Particle Motion on Qdots:

In a similar experiment as above (directed motion) in vitro models were placed in 8 well plates with both magnetic particles (20 μL fluidMAG-CMX 150 nm, Chemicell Berlin, Germany) and either Qdot 655 (10 μL Qdot 655 nm biotin, invitrogen-molecular probe, Eugene, Oreg.) or Qtracker 655 (10 μL Qtracker 655 nm. Invitrogen-molecular probe, Eugene, Oreg.). Videos were taken for single particle tracking anaylsis on the Qdot 655 or Qtracker 655 particles before and during a magnetic field present. The magnetic field was provided by a neodymium-iron-boron permanent magnet having a volume of one cubic centimeter placed outside each individual well.

Results:

Qdots have Increased Transport in Models of CF Mucus and Alginate Biofilms Under Increased Thermal Properties Investigated was the influence of thermal energy on particle motion and transport in models of mucus and alginate biofilms to mimic CF biological barriers using single particle tracking. The composition of these media is fully described in the methods section. The particle tracking experiments and imaging parameters are also fully described in the methods section. Briefly, we observed Qdot 655 particles using a widefield microscope at 100× magnification and at 100 frames per second giving excellent temporal resolution of particle movement. Analysis of transport was performed on Matlab image analysis program. FIGS. 6a-6c and 7a-7b indicate that temperature has an effect on the motion of nanoparticles in an alginate biofilm and mucin model. Diffusion coefficients for Qdot 655 in alginate model were compared (FIG. 4). Transport at lower temperatures appears very hindered and particles, though mobile, do not follow random diffusion trajectories (FIG. 6a-6b, 7a). Rather, at low temperatures, particles tend to move within pockets and have significantly restricted transport outside of these regions (FIG. 6a, 7a). Such transport increase by thermal energy suggests that both bulk heating and localized heating may have significant effects on transport and illustrate the potential for nanoparticles that exhibit thermal properties to increase diffusion.

Magnetic Nanoparticles have Increased Bulk Transport When Exposed to a Magnetic Field:

Transport of the magnetic nanoparticles was significantly influenced by the application of a magnetic field in the alginate model. We illustrate this influence qualitatively by taking bulk transport photo montage (FIG. 9a which is a line drawing based on the photo montage) showing bulk transport moving toward the permanent magnet (rectangle). Quantification of bulk transport in FIG 9b was performed by measuring the change in intensity over a 30 second time either in the presence of or not in the presence of a magnetic field (FIG. 9b). The quantification of transport was found to have increased by 80% once a magnetic field is present.

To further quantify bulk transport properties studies were conducted in side-by-side diffusion cells. Permeation rates during magnetically enhanced transport were significantly higher than control.

Magnetic Nanoparticles have Increased Transport at a Single Particle Transport Under a Magnetic Field:

After seeing modified transport of nanoparticles at a bulk level it was of interest to see if the velocity changed at a single particle level. Fluorescent magnetic nanoparticles with different functional groups (chitosan, lipid, and carboxymethyldextran) were added to alginate biofilm model. Transport was evaluated using single particle tracking and quantified by using a Matlab algorithm resulting in a MSD plot based on directed with diffusion given by the equation $MSD=(vt)^2+4Dt$, where v is the velocity, t is time, and D is diffusion. The velocity coefficient for all particles with or without a magnetic field in the alginate model was graphed based on their sizes (150 nm or 250 nm; FIG. 11-12). Increased transport was seen for all particles no matter size nor the functional group once the particles were exposed to a magnetic. At 250 nm all increased velocity coefficients were statistically significant ($p \leq 0.05$), while at 1 50 nm all but the chitosan functional group statistically relevant ($p \leq 0.05$) increases once a magnetic field was prescient, despite large error bars. This was seen in mucin as well (data not shown).

Magnetic Nanoparticles Form Channels for Unconjugated Drug Delivery:

Testing of bulk transport of magnetic nanoparticles was investigated by lining a petri-dish with alginate and by adding a droplet (10 microliters) of magnetic nanoparticles thereto. A neodymium-iron-boron permanent magnet having a volume of one cubic centimeter was placed outside of the petri-dish. Images were taken with a digital camera. During studies of bulk transport of magnetic nanoparticles images were taken of transport through biofilm model (FIG. 13). Channels were visualized following magnetic transport of nanoparticles through alginate. Such open channels can provide additional pathways through which drug can be transported and delivered.

The above illustrates the value of magnetic nanoparticles for drug delivery through biological barriers seen in CF patients. Magnetic nanoparticles can be directed through a visco-elastic medium to help transport drugs to a desired location. As well it was seen that channels were formed by such directed movement and that these channels help unconjugated particles move within the channels. Unconjugated particles are able to more than double there movement through the biological barrier models by the influence of the magnetic nanoparticle motion. Not only are the magnetic nanoparticles having increased movement but their movement can help propel a drug towards a site. Further studies are needed to see if such movement is significant in mucin and at different mixing steps (i.e. if particles are mixed with magnetic nanoparticles before adding to models). These findings show the potential for drug delivery enhancement by magnetic nanoparticles even without having a drug conjugated to the surface as previously described.

EXAMPLE 3

This Example illustrates enhancing of particle transport through a biofilm model using static magnetic fields and non-magnetic drug particles. Drug delivery is enhanced by the magnetic pull of magnetic nanoparticles and their formation of channels:

To further investigate the effect of channel formation by nanoparticles on drug delivery we used single particle tracking on Qdots 655 and Qtracker 655 in both a mucin and alginate model. Magnetic nanoparticles and either Qdot 655 or Qtracker 655 were mixed separately with either mucin or alginate model and the Qdots were tracked at a single particle level with or without a magnetic field. Qtracker 655 that are only coated in PEG polymer were found to have roughly twice the movement as Qdot 655 which are functionalized with biotin, indicating an influence of functional groups on movement in alginate, though this was not seen in mucin. Particles were pulled under a magnetic field under the influence of motion by magnetic nanoparticles and the channels that are formed. Such motion was found to be relevant in the alginate models for both particles ($p \leq 0.05$).

Methods

CF Mucin Model: Pig gastric mucin (type II, lyophilized, Sigma), will be used as a screening model for particle systems. Mucin solutions were prepared by a modified reconstitution procedure as described above for use as a model for CF mucus at 20% concentration.

Alginate Model:

Concentration for the content of alginate biogels secreted by in vivo samples of *P. aeruginosa* infections for alginate gels was: Alginate concentration will be 2% (w/v) as described above and the bivalent cation concentration (calcium ions) range from 0.5 to 1.8 mM as described above.

These in vitro models of biofilms and mucus barriers were placed in 8 well plates with both magnetic particles (20 µL fluidMAG-CMX 150 nm dia., Chemicell Berlin, Germany) and either Qdot 655 (10 µL Qdot 655 nm biotin, Invitrogen-molecular probes, Invitrogen Corp., Eugene, Oreg.) or Qtracker 655 (10 µL Qtracker 655 nm. Invitrogen-molecular probes, Eugene, Oreg.). The concentrations used were 2 microM in 10 microliters of Qdots and 1.2 mg/mL of magnetic nanoaprticles. The magnetic field was provided by a neodymium-iron-boron permanent magnet having a volume of one cubic centimeter placed outside each individual well. The magnetic nanoparticles were added to 1 mL of biofilm or mucin model and allowed to mix overnight in a shaker and then the Qdots were added and allowed to mix in a shaker for one hour, until well mixed. Videos were taken for single particle tracking analysis on the Qdot 655 or Qtracker 655 non-magnetic particles before and during a magnetic field present where a magnetic field was placed on the outside of each individual well.

The Qdot (quantum dot) non-magnetic particles were used as models of drug nanoparticles. These Qdots were highly fluorescent and allows easy imaging and particle tracking using microscopic methods. The Qdots were not magnetic, and therefore are not directly influenced by the external magnetic fields. The present of the magnetic nanoparticles in the mixture (non-fluorescent) will respond to the magnetic fields directly as shown in previous examples.

To monitor the influence of the magnetic nanoparticles and magnetic field influence on non-magnetic particles, we then used single particle tracking of the Qdots in the presence and absence of a static magnetic field.

Single Particle Tracking: Wide field imaging for single particle tracking for Quantum dots (Qtracker 655 nm, Qdot 655 nm Biotin, Invitrogen-molecular probes, Eugene, Oreg.) and magnetic particles (nano-screenMAG chitosan, cmx, and lipid, Chemicell Berlin, Germany) was performed using an Olympus IX71 inverted microscope equipped with a 100°—oil objective. Excitation was provided by a mercury lamp with a 543 nm BP filter. Emission collected by an Andor iXon electron multiplying CCD (emCCD) camera. The back-projected CCD pixel size is 160 nm and images are acquired at 100 frames/s. Typically, a region of interest of 128×128 pixels was selected for imaging. Analysis of the acquired image series will be performed as described previously 91. Images will be processed using DIPImage (Delft University of Technology) and tracking routines written in MATLAB (The MathWorks, Inc.) that calculate the center of intensity in a region around the maximum at each time step. These algorithms can explicitly account for the intermittent QD fluorescence, or blinking that. From these trajectories, the mean square displacement (MSD) as a function of time interval ($\Delta t$) will be calculated. The resulting MSD plot is fitted to the equation for free diffusion: MSD=offset+4D$\Delta t$, where MSD is the mean square displacement, D is the diffusion coefficient, $\Delta t$ is the time interval, and offset is related to the localization accuracy. Other modes of motion can be determined from these plots, including velocity. Localization accuracy of the system is determined by imaging QDots bound to a coverslip for 1,000 frames with 20 ms exposure, which typically yields accurate localization of the particle center of mass to within 12 nm.

FIG. 14 shows that the non-magnetic nanoparticles had large increases in their transport velocities when a magnetic field was applied to the physical mixture. This was observed in both alginate and mucin media and velocities in a magnetic field relative to velocities without magnetic fields were on the order of 10 to 40 fold higher for the non-magnetic particles. The surface chemistry of the non-magnetic particles also contributed to the magnitude of the velocity increases.

The above Examples illustrate the value of magnetic nanoparticles for drug delivery through biological barriers seen in CF patients. Magnetic nanoparticles can be directed through a visco-elastic medium to help transport drugs to a desired location. As well it was seen that channels were formed by such directed movement and that these channels help unconjugated non-magnetic particles move within the channels. Unconjugated non-magnetic particles are able to more than double there movement through the biological barrier models by the influence of the magnetic nanoparticle motion. Not only are the magnetic nanoparticles having increased movement but their movement can help propel a drug towards a site. The Example above shows the potential for drug delivery enhancement by magnetic nanoparticles even without having a drug conjugated to the surface.

EXAMPLE 4

This Example illustrates use of magnetic nanoaprticles in illustrative embodiments of a transdermal patch. FIG. 15 schematically shows a transdermal patch on an arm of a user. FIG. 16 shows a transdermal patch comprising a backing layer, a drug reservoir layer, adhesive in which magnetic nanoaprticles are embedded and a releasable liner. FIG. 17 shows a transdermal patch comprising a backing layer, a layer including a drug, magnetic nanoparticles and adhesive, and a liner. FIG. 18 shows a transdermal patch comprising a foam backing and adhesive layer, an enlarged reservoir including a drug and magnetic nanoparticles.

FIG. 19 illustrates magnetic nanoparticles being transported or pulled across the skin (stratum corneum) and through sweat pores under the influence of a static magnetic field provided by horseshoe magnet shown, which can comprise a permanent magnet adjacent the user's arm on a side opposite from the transdermal patch.

FIG. 20 illustrates magnetic nanoparticles being transported across the skin (stratum corneum) under the influence of an oscillating magnetic field provided by coil in which the user's arm is inserted (see FIG. 15) and of a static magnetic field provided by horseshoe magnet shown, which can comprise a permanent magnet adjacent to the user's arm on a side opposite from the transdermal patch.

Although the invention has been described with respect to certain illustrative embodiments thereof, those skilled in the art will appreciate that the invention is not limited to these embodiments and that changes and modifications can be made therein within the scope of the invention as set forth in the appended claims.

The invention claimed is:

1. A method of transporting a drug to a target bacterial infection of epithelial tissue in a patient's body where access to the target bacterial infection site is impaired by the presence of a biological barrier comprising at least one of a mucus barrier, an alginate barrier and a microbial biofilm barrier, comprising administering a plurality of magnetic nanoparticles adjacent to the biological barrier, said magnetic nanoparticles carrying a drug, and providing a nanoparticle-moving magnetic field proximate to the target bacterial infection site in a manner that transports the plurality of drug-carrying nanoparticles to traverse through the barrier to reach the target bacterial infection site.

2. The method of claim 1 wherein the drug is chemically or physically attached to the magnetic nanoparticles by at least one of surface functionalization, bioconjugation, and encapsulation.

3. The method of claim 1 wherein the nanoparticle-moving magnetic field is a static magnetic field that imparts nanoparticle motion to transport the drug-carrying nanoparticles through the barrier to the target bacterial infection site.

4. The method of claim 1 wherein the magnetic field is generated by a device outside the patient's body.

5. The method of claim 1 wherein an alternating magnetic field is provided when the drug-carrying nanoparticles are proximate to the target bacterial infection site to heat and/or oscillate the nanoparticles.

6. The method of claim 5 wherein the alternating magnetic field is generated by a device outside the patient's body.

7. The method of claim 5 wherein the alternating magnetic field proximate to the target bacterial infection site is used to release the drug.

8. A method of transporting a drug to a target bacterial infection of epithelial tissue in an airway of a patient where access to the target bacterial infection site is impaired by the presence of a biological barrier comprising at least one of a mucus barrier, an alginate barrier and a microbial biofilm barrier at the target bacterial infection site of the airway, comprising administering microparticles adjacent to the biological barrier, wherein the said microparticles comprise a plurality of magnetic nanoparticles carrying the drug, wherein the said drug-carrying magnetic nanoparticles are dispersed from the microparticles and are deposited at the biological barrier, and providing a nanoparticle-moving magnetic field generated by a device outside of the patient's body that transports the drug-carrying magnetic nanoparticles to traverse through the biological barrier to reach the target bacterial infection site.

9. The method of claim 8 wherein the nanoparticle-moving magnetic field is a static magnetic field that imparts nanoparticle motion to transport the drug-carrying magnetic nanoparticles through the biological barrier to the target bacterial infection site.

10. The method of claim 9 wherein an alternating magnetic field is also provided when the drug-carrying magnetic nanoparticles are proximate to the target bacterial infection site to heat and/or oscillate the nanoparticles.

11. The method of claim 10 wherein the alternating magnetic field is generated by a device outside the patient's body.

12. The method of claim 10 wherein the alternating magnetic field proximate to the target bacterial infection site is used to release the drug.

13. The method of claim 10 wherein the static magnetic field and the alternating magnetic field are provided concurrently.

14. The method of claim 8 wherein the is target bacterial infection site resides in a diseased lung.

15. A method of delivering a drug to a target bacterial infection site of a patient's body, comprising delivering magnetic nanoparticles conjugated to the drug to an interior passage of the body where they are deposited adjacent the target bacterial infection site, providing a static magnetic field in a manner to transport the deposited magnetic nanoparticles conjugated to the drug to the target bacterial infection site and then using an alternating magnetic field proximate to the target bacterial infection site to release said drug at the target bacterial infection site.

16. A method of transporting a drug through a patient's skin, comprising providing a plurality of drug-carrying magnetic nanoparticles proximate to the skin at an exterior region of the patient's body and providing a nanoparticle-moving magnetic field in such relation to said exterior region the patient's body as to transport the plurality of drug-carrying nanoparticles through the stratum corneum to deliver the drug-carrying magnetic nanoparticles beneath the stratum corneum.

* * * * *